(12) United States Patent
King et al.

(10) Patent No.: US 11,052,244 B2
(45) Date of Patent: Jul. 6, 2021

(54) BIOELECTRIC HYDROGELS AND METHODS OF MANUFACTURE AND USE

(71) Applicant: Vomaris Innovations, Inc., Tempe, AZ (US)

(72) Inventors: Wendell King, Pillager, MN (US); Joseph Del Rossi, Tempe, AZ (US); Troy Paluszcyk, Tempe, AZ (US)

(73) Assignee: Vomaris Innovations, Inc., Tempe, AZ (US)

( * ) Notice: Subject to any disclaimer, the term of this patent is extended or adjusted under 35 U.S.C. 154(b) by 611 days.

(21) Appl. No.: 15/738,413

(22) PCT Filed: Jul. 1, 2016

(86) PCT No.: PCT/US2016/040827
§ 371 (c)(1),
(2) Date: Dec. 20, 2017

(87) PCT Pub. No.: WO2017/004582
PCT Pub. Date: Jan. 5, 2017

(65) Prior Publication Data
US 2018/0169407 A1    Jun. 21, 2018

Related U.S. Application Data

(60) Provisional application No. 62/187,535, filed on Jul. 1, 2015, provisional application No. 62/339,500, filed on May 20, 2016.

(51) Int. Cl.
*A61N 1/20*    (2006.01)
*A61N 1/04*    (2006.01)
(Continued)

(52) U.S. Cl.
CPC ............. *A61N 1/205* (2013.01); *A61L 31/145* (2013.01); *A61N 1/0468* (2013.01);
(Continued)

(58) Field of Classification Search
CPC ...... A61N 1/205; A61N 1/0468; A61L 31/145
(Continued)

(56) References Cited

U.S. PATENT DOCUMENTS

2011/0087315 A1* 4/2011 Richardson-Burns ........................ A61N 1/0536
607/116

FOREIGN PATENT DOCUMENTS

| EP | 0323711 A1 | 7/1989 |
| WO | 2014/178945 A1 | 11/2014 |
| WO | 2017/004582 A1 | 1/2017 |

OTHER PUBLICATIONS

International Search Report and Written Opinion for International Application No. PCT/US2016/040827 dated Sep. 8, 2016.

* cited by examiner

*Primary Examiner* — Nadia A Mahmood
(74) *Attorney, Agent, or Firm* — K&L Gates LLP; Louis C. Cullman; Hal Gibson

(57) ABSTRACT

The present disclosure relates to a bioelectric hydrogel. In one embodiment, a hydrogel comprises a hydrophilic polymer base and one or more biocompatible electrodes configured to generate at least one of a low level electric field (LLEF) or low level electric current (LLEC). The hydrogel is configured to provide a three-dimensional energy source within the hydrogel or to devises proximate to the hydrogel.

10 Claims, 11 Drawing Sheets

(51) Int. Cl.
   *A61L 31/14* (2006.01)
   *A61K 9/00* (2006.01)
   *A61N 1/30* (2006.01)
(52) U.S. Cl.
   CPC .......... *A61N 1/0484* (2013.01); *A61K 9/0009* (2013.01); *A61N 1/303* (2013.01)
(58) Field of Classification Search
   USPC ........................................................... 607/2
   See application file for complete search history.

BIOELECTRIC HYDROGELS AND METHODS OF MANUFACTURE AND USE

RELATED APPLICATIONS

This application is an application under 35 U.S.C. § 371 of International Patent Application PCT/US2016/040827 filed on Jul. 1, 2016, which claims the benefit of U.S. provisional patent application No. 62/187,535, filed Jul. 1, 2015 and U.S. Provisional Patent Application 62/339,500, filed May 20, 2016; the disclosures of each of which are incorporated herein by reference in their entirety.

FIELD

Biologic tissues and cells are affected by electrical stimulus. Accordingly, apparatus and techniques for applying electric stimulus to biological tissue and cells have been developed to address a number of medical issues. The present specification relates to bioelectric hydrogels and methods of manufacture and use thereof.

SUMMARY

Disclosed and claimed herein are systems, devices, and methods comprising at least one hydrogel. An embodiment comprises a hydrogel, for example a conductive hydrogel, comprising a hydrophilic polymer base and one or more biocompatible electrodes comprising an array configured to generate at least one of a low level electric field (LLEF) or low level electric current (LLEC). The hydrogel can be of various viscosities to allow the hydrogel to be shaped or molded into an object or formed to the human body such as an arm, leg, torso, face, etc. Two arrays can be suspended in hydrogels, for example in two hydrogels having different properties, for example having different viscosities.

The biocompatible electrodes can comprise a first bioelectric element comprising an array of a first microparticle formed from a first conductive material, and a second bioelectric element comprising an array of a second microparticle formed from a second conductive material.

In embodiments, one of the arrays can comprise microcells or electrodes embedded in or applied to a substrate, for example a dressing.

Embodiments are directed toward methods for treating a patient with the disclosed hydrogel systems and devices. Further embodiments are directed toward methods for manufacturing a disclosed system or device, comprising coupling a hydrogel comprising a hydrophilic polymer base and one or more biocompatible electrodes configured to generate at least one of a LLEF or LLEC to an area where an injury is present.

Certain aspects utilize an external power source such as AC or DC power, or pulsed RF. In one embodiment, the electrical energy is derived from the dissimilar metals creating a battery at each microcell/microcell or electrode/electrode interface, whereas those embodiments with an external power source may require conductive electrodes in a spaced apart configuration to predetermine the electric field shape and strength.

Disclosed systems and devices can generate a localized electric field in a pattern determined by the physical orientation of the array or, for example, by the viscosity of the gel.

Disclosed herein are systems, devices, and methods for use in treatment of subjects, for example around or about a muscle or muscle group, for example the deltoids, the triceps, the biceps, the quadriceps, the calf, the shoulder, the abdominals, the back, or the like.

Disclosed embodiments can reduce or prevent muscle damage (for example such as can occur during a workout or athletic performance), improve muscle function, improve athletic performance, and accelerate muscle recovery.

Disclosed herein are systems, devices, and methods for use in treatment of subjects, for example treatment of tissue around or about a joint of the body, for example the knee, the elbow, or the like. Disclosed herein are systems, devices, and methods for use in treatment of subjects, for example around the face, the neck, the chest, the stomach, the arm, the back, the buttocks, the thigh, the calf, the foot, or the like.

Further aspects include a method of directing cell migration using a device disclosed herein. These aspects include methods of improving re-epithelialization.

Further aspects include methods of increasing glucose uptake as well as methods of increasing cellular thiol levels. Additional aspects include a method of energizing mitochondria.

Further aspects include a method of stimulating cellular protein expression.

Further aspects include a method of stimulating cellular DNA synthesis.

Further aspects include a method of stimulating cellular $Ca^{2+}$ uptake.

Aspects of the invention include devices and methods for increasing capillary density.

Embodiments include devices and methods for increasing transcutaneous partial pressure of oxygen. Further embodiments include methods and devices for treating or preventing pressure ulcers.

In embodiments, these systems, devices, and methods can increase cell migration, ATP production, and angiogenesis, thus accelerating the healing process. Disclosed systems, devices, and methods can also reduce bacterial population and/or proliferation in and around injuries. The system, devices, and methods can also increase cellular glucose uptake, thus increasing availability of cellular energy and athletic performance.

Additional aspects include methods of preventing bacterial biofilm formation. Aspects also include a method of reducing microbial or bacterial proliferation, killing microbes or bacteria, killing bacteria through a biofilm layer, or preventing the formation of a biofilm. Embodiments include methods using devices disclosed herein in combination with antibiotics for reducing microbial or bacterial proliferation, killing microbes or bacteria, killing bacteria through a biofilm layer, or preventing the formation of a biofilm.

Further aspects include methods of treating diseases related to metabolic deficiencies, such as diabetes, or other diseases wherein the patient exhibits a compromised metabolic status.

Embodiments can also increase integrin expression and accumulation in treatment areas.

Certain embodiments are designed for universal conformability with any area of the body, for example a flat area or a contoured area. In embodiments the systems, devices, and methods include fabrics, for example clothing or dressings, that comprise one or more biocompatible electrodes configured to generate at least one of a low level electric field (LLEF) or low level electric current (LLEC). In embodiments the dressings are configured to conform to the area to be treated, for example by producing the dressing in particular shapes including "slits" or discontinuous regions. In embodiments the dressing can be produced in a U shape wherein the "arms" of the U are substantially equal in length as compared to the "base" of the U. In embodiments the dressing can be produced in a U shape wherein the "arms" of the U are substantially longer in length as compared to the "base" of the U. In embodiments the dressing can be produced in a U shape wherein the "arms" of the U are substantially shorter in length as compared to the "base" of the U. In embodiments the dressing can be produced in an X shape wherein the "arms" of the X are substantially equal in length.

The systems and devices can comprise corresponding or interlocking perimeter areas to assist the devices in maintaining their position on the patient and/or their position relative to each other. In certain embodiments, the systems and devices can comprise a port or ports to provide access to the treatment area beneath the device.

Certain embodiments can comprise a solution or formulation comprising an active agent and a solvent or carrier or vehicle.

DETAILED DESCRIPTION

Figure 1:
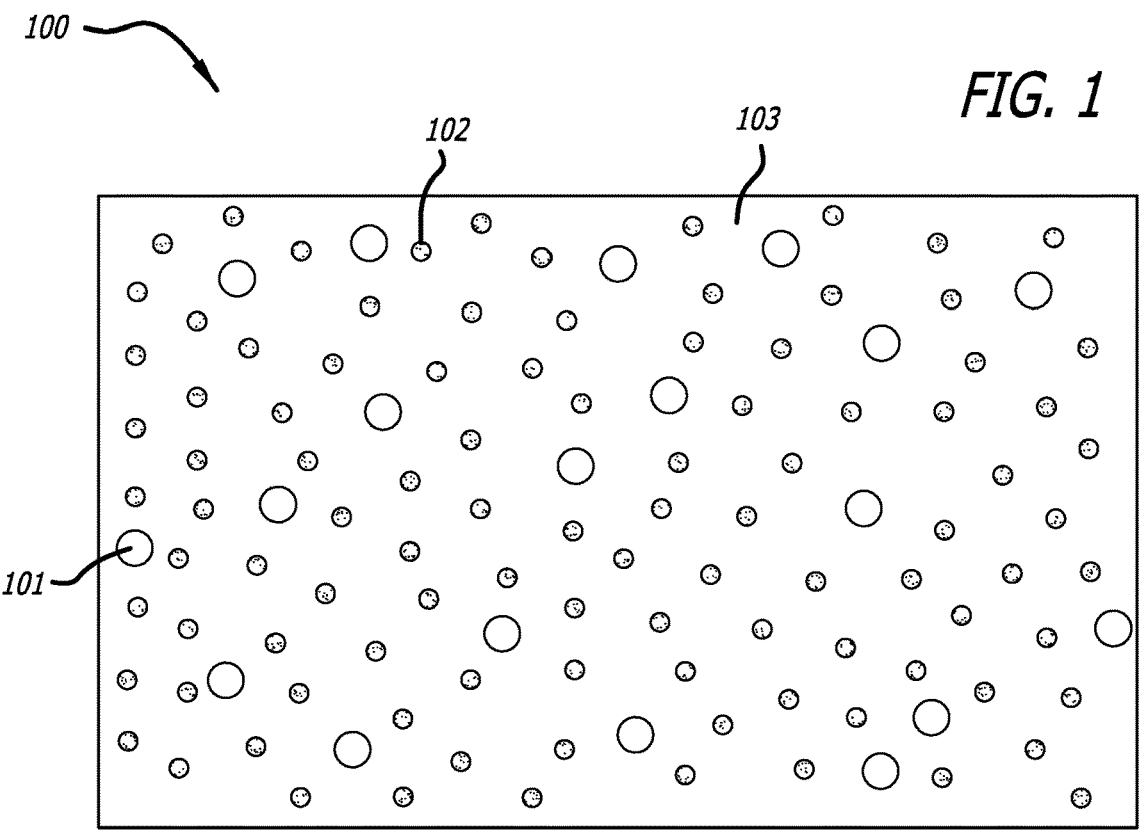
FIG. 1 depicts a graphical representation of a bioelectric hydrogel according to one or more embodiments disclosed herein.

Embodiments disclosed herein comprise systems and devices that can provide a low level electric field (LLEF) to a tissue or organism (thus a "LLEF system") or, when brought into contact with an electrically conducting material, can provide a low level electric micro-current (LLEC) to a tissue or organism (thus a "LLEC system"). Thus, in embodiments a LLEC system is a LLEF system that is in contact with an electrically conducting material, for example a liquid material. In certain embodiments, the micro-current or electric field can be modulated, for example, to alter the duration, size, shape, field depth, duration, current, polarity, or voltage of the system. For example, it can be desirable to employ an electric field of greater strength or depth in an area to achieve optimal treatment. In embodiments the watt-density of the system can be modulated.

Definitions

"Activation agent" as used herein means a composition useful for maintaining a moist environment within and about the skin. Activation agents can be in the form of gels or liquids. Activation agents can be conductive. Activation gels can also be antibacterial. In one embodiment, an activation agent can be a liquid such as sweat or topical substance such as petroleum jelly (for example with a conductive component added).

"Affixing" as used herein can mean contacting a patient or tissue with a device or system disclosed herein. In embodiments "affixing" can comprise the use of straps, elastic, etc.

"Antimicrobial agent" as used herein refers to an agent that kills or inhibits the growth of microorganisms. One type of antimicrobial agent can be an antibacterial agent. "Antibacterial agent" or "antibacterial" as used herein refers to an agent that interferes with the growth and reproduction of bacteria. Antibacterial agents are used to disinfect surfaces and eliminate potentially harmful bacteria. Unlike antibiotics, they are not used as medicines for humans or animals, but are found in products such as soaps, detergents, health and skincare products and household cleaners. Antibacterial agents may be divided into two groups according to their speed of action and residue production: The first group contains those that act rapidly to destroy bacteria, but quickly disappear (by evaporation or breakdown) and leave no active residue behind (referred to as non-residue-producing). Examples of this type are the alcohols, chlorine, peroxides, and aldehydes. The second group consists mostly of newer compounds that leave long-acting residues on the surface to be disinfected and thus have a prolonged action (referred to as residue-producing). Common examples of this group are triclosan, triclocarban, and benzalkonium chloride. Another type of antimicrobial agent can be an anti-fungal agent that can be used with the devices described herein.

"Applied" or "apply" as used herein refers to contacting a surface with a conductive material, for example printing, painting, or spraying a conductive ink on a surface. Alternatively, "applying" can mean contacting a patient or tissue or organism with a device or system disclosed herein.

"Conductive material" as used herein refers to an object or type of material which permits the flow of electric charges in one or more directions. Conductive materials can comprise solids such as metals or carbon, or liquids such as conductive metal solutions and conductive gels. Conductive materials can be applied to form at least one matrix. Conductive liquids can dry, cure, or harden after application to form a solid material.

"Discontinuous region" as used herein refers to a "void" in a material such as a hole, slot, or the like. The term can mean any void in the material though typically the void is of a regular shape. A void in the material can be entirely within the perimeter of a material or it can extend to the perimeter of a material.

"Dots" as used herein refers to discrete deposits of dissimilar reservoirs that can function as at least one battery cell. The term can refer to a deposit of any suitable size or shape, such as squares, circles, triangles, lines, etc. The term can be used synonymously with, microcells, microspheres, etc. "Microspheres" refers to are small spherical particles, with diameters in the micrometer range (typically 1 μm to 3000 μm (3 mm)). Microspheres are sometimes referred to as microparticles. Microspheres can be manufactured from various natural and synthetic materials. The term can be used synonymously with, microballoons, beads, particles, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand.

"Galvanic cell" as used herein refers to an electrochemical cell with a positive cell potential, which can allow chemical energy to be converted into electrical energy. More particularly, a galvanic cell can comprise a first reservoir serving as an anode and a second, dissimilar reservoir serving as a cathode. Each galvanic cell can store chemical potential energy. When a conductive material is located proximate to a cell such that the material can provide electrical and/or ionic communication between the cell elements the chemical potential energy can be released as electrical energy. Accordingly, each set of adjacent, dissimilar reservoirs can function as a single-cell battery, and the distribution of multiple sets of adjacent, dissimilar reservoirs within the apparatus can function as a field of single-cell batteries, which in the aggregate forms a multiple-cell battery distributed across a surface. In embodiments utilizing an external power source the galvanic cell can comprise electrodes connected to an external power source, for example a battery or other power source. In embodiments that are externally-powered, the electrodes need not comprise dissimilar materials, as the external power source can define the anode and cathode. In certain externally powered embodiments, the power source need not be physically connected to the device.

"Matrix" or "matrices" or "array" or "arrays" as used herein refer to a pattern or patterns, such as those formed by electrodes on a surface, such as a fabric or a fiber, or the like. Matrices can also comprise a pattern or patterns within a solid or liquid material or a three dimensional object. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Reduction-oxidation reaction" or "redox reaction" as used herein refers to a reaction involving the transfer of one or more electrons from a reducing agent to an oxidizing agent. The term "reducing agent" can be defined in some embodiments as a reactant in a redox reaction, which donates electrons to a reduced species. A "reducing agent" is thereby oxidized in the reaction. The term "oxidizing agent" can be defined in some embodiments as a reactant in a redox reaction, which accepts electrons from the oxidized species. An "oxidizing agent" is thereby reduced in the reaction. In various embodiments a redox reaction produced between a first and second reservoir provides a current between the dissimilar reservoirs. The redox reactions can occur spontaneously when a conductive material is brought in proximity to first and second dissimilar reservoirs such that the conductive material provides a medium for electrical communication and/or ionic communication between the first and second dissimilar reservoirs. In other words, in an embodiment electrical currents can be produced between first and second dissimilar reservoirs without the use of an external battery or other power source (e.g., a direct current (DC) such as a battery or an alternating current (AC) power source such as a typical electric outlet). Accordingly, in various embodiments a system is provided which is "electrically self contained," and yet the system can be activated to produce electrical currents. The term "electrically self contained" can be defined in some embodiments as being capable of producing electricity (e.g., producing currents) without an external battery or power source. The term "activated" can be defined in some embodiments to refer to the production of electric current through the application of a radio signal of a given frequency or through ultrasound or through electromagnetic induction. In other embodiments, a system can be provided which comprises an external battery or power source. For example, an AC power source can be of any wave form, such as a sine wave, a triangular wave, or a square wave. AC power can also be of any frequency such as for example 50 Hz or 60 HZ, or the like. AC power can also be of any voltage, such as for example 120 volts, or 220 volts, or the like. In embodiments an AC power source can be electronically modified, such as for example having the voltage reduced, prior to use.

"Stretchable" as used herein refers to the ability of embodiments that stretch without losing their structural integrity. That is, embodiments can stretch to accommodate irregular skin surfaces or surfaces wherein one portion of the surface can move relative to another portion.

"Treatment" as used herein can include the use of disclosed embodiments on muscles to prevent, reduce, or repair muscle damage. Treatment can also include the use of disclosed embodiments on the skin, eyes, etc. Treatment can include use on an injury, for example a wound.

"Viscosity" as used herein refers to a measurement of a fluid's resistance to gradual deformation by shear stress or tensile stress. That is, embodiments can accommodate multiple viscosity variations without losing structural integrity, wherein one embodiment can be a liquid or a solid material.

LLEC/LLEF Systems, Devices, and Methods of Manufacture

Embodiments of the LLEC or LLEF system disclosed herein can comprise electrodes or dots or microcells. Each electrode or dot or microcell can be or comprise a conductive metal. In embodiments, the electrodes or microcells can comprise any electrically-conductive material, for example, an electrically conductive hydrogel, metals, electrolytes, superconductors, semiconductors, plasmas, and nonmetallic conductors such as graphite and conductive polymers. Electrically conductive metals can comprise silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrode can be solid, coated or plated with a different metal such as aluminum, gold, platinum or silver.

In certain embodiments, reservoir or electrode geometry can comprise circles, polygons, lines, zigzags, ovals, stars, or any suitable variety of shapes. This provides the ability to design/customize surface electric field shapes as well as depth of penetration. For example. In embodiments it can be desirable to employ an electric field of greater strength or depth in an area where skin is thicker to achieve optimal treatment.

Reservoir or electrode or dot sizes and concentrations can vary, as these variations can allow for changes in the properties of the electric field created by embodiments of the invention. Certain embodiments provide an electric field at about, for example, 0.5-5.0 V at the device surface under normal tissue loads with resistance of 100 to 100K ohms.

In embodiments, systems and devices disclosed herein comprise patterns of micro-batteries that create a field between each dot pair. In embodiments, the unique field is very short, e.g. in the range of physiologic electric fields. In embodiments, the direction of the electric field produced by devices disclosed herein is omnidirectional within a three dimensional material.

Embodiments disclosed herein can comprise patterns or randomly dispersed microcells, for example within a hydrogel or on a substrate. The patterns can be designed to produce an electric field, an electric current, or both, over and through a three dimensional material or tissue such as human skin. In embodiments the pattern can be designed to produce a specific size, strength, density, shape, or duration of electric field or electric current. In embodiments reservoir or dot size and separation can be altered.

In embodiments devices disclosed herein can apply an electric field, an electric current, or both, wherein the field, current, or both can be of varying size, strength, density, shape, or duration in different areas of the embodiment. In embodiments, by micro-sizing the electrodes or reservoirs, the shapes of the electric field, electric current, or both can be customized, increasing or decreasing very localized watt densities and allowing for the design of patterns of electrodes or reservoirs wherein the amount of electric field over a tissue can be designed or produced or adjusted based upon feedback from the tissue or upon an algorithm within sensors operably connected to the embodiment and a control module. The electric field, electric current, or both can be stronger in one zone and weaker in another. The electric field, electric current, or both can change with time and be modulated based on treatment goals or feedback from the tissue or patient. The control module can monitor and adjust the size, strength, density, shape, or duration of electric field or electric current based on material parameters or tissue parameters. For example, embodiments disclosed herein can produce and maintain very localized electrical events. For example, embodiments disclosed herein can produce specific values for the electric field duration, electric field size, electric field shape, field depth, current, polarity, and/or voltage of the device or system.

Devices disclosed herein can generate a localized electric field in a pattern determined by the distance and physical orientation of the cells or electrodes. Effective depth of the electric field can be predetermined by the orientation and distance between the cells or electrodes.

Embodiments can comprise a hydrogel. A hydrogel is a network of polymer chains that are hydrophilic. Hydrogels are highly absorbent natural or synthetic polymeric networks. Hydrogels can be configured to contain a high percentage of water (e.g. they can contain over 90% water). Hydrogels can possess a degree of flexibility very similar to natural tissue, due to their significant water content. A hydrogel can be configured in a variety of viscosities. Viscosity is a measurement of a fluid or material's resistance to gradual deformation by shear stress or tensile stress. In embodiments the electrical field can be extended through a semi-liquid hydrogel with a low viscosity such an ointment or a cellular culture medium. In other embodiments the electrical field can be extended through a solid hydrogel with a high viscosity such as a Petri dish, clothing, or material used to manufacture a prosthetic. In general, the hydrogel described herein may be configured to a viscosity of between about 0.5 Pa·s and greater than about $10^{12}$ Pa·s. In embodiments the viscosity of a hydrogel can be, for example, between 0.5 and $10^{12}$ Pa·s, between 1 Pa·s and $10^6$ Pa·s, between 5 and $10^3$ Pa·s, between 10 and 100 Pa·s, between 15 and 90 Pa·s, between 20 and 80 Pa·s, between 25 and 70 Pa·s, between 30 and 60 Pa·s, or the like. In embodiments, the hydrogel can comprise hydrophobic properties.

Dissimilar metals used to make a LLEC or LLEF system disclosed herein can be silver and zinc. In certain embodiments the electrodes are coupled with a non-conductive material to create a random dot pattern or a uniform dot pattern within a hydrogel, most preferably an array or multi-array of voltaic cells that do not spontaneously react until they contact an electrolytic solution. Sections of this description use the terms "coated," "plated," or "printed" with "ink," but it is to be understood that a dot in a hydrogel may also be a solid microsphere of conductive material. The use of any suitable means for applying a conductive material is contemplated. In embodiments "coated," "plated," or "printed" can comprise any material such as a solution suitable for forming an electrode on a surface of a microsphere such as a conductive material comprising a conductive metal.

In another embodiment, microspheres can be formed, coated, and plated by printing. In embodiments, printing devices can be used to produce LLEC or LLEF systems disclosed herein. For example, inkjet or "3D" printers can be used to produce embodiments. In certain embodiments the binders or inks used to produce LLEC or LLEF systems disclosed herein can comprise, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicon, can be added to enhance, for example, scar reduction. Such materials can also be added to the spaces between reservoirs.

Figure 2:
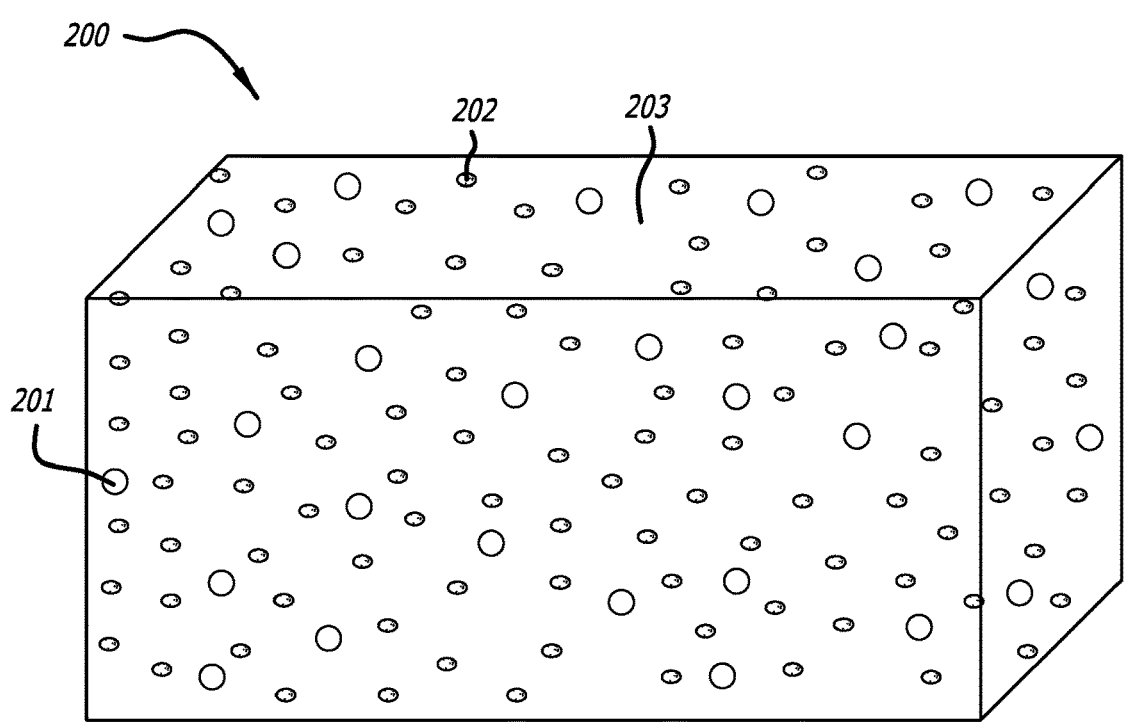
FIG. 2 depicts a three dimensional representation of a bioelectric hydrogel according to one or more embodiments.

FIG. 1 depicts a graphical representation of a bioelectric hydrogel according to one or more embodiments. In FIG. 1, the dissimilar first electrode 101 and second electrode 102 are in a desired hydrophilic polymer base 103 of a hydrogel 100, for example an ointment or cellular culture medium. In one embodiment a hydrogel 100 is a material of a LLEC or LLEF system that comes into direct contact with an area to be treated such as a skin surface or within the hydrogel for cellular culture. Hydrogel 100 can also be configured or shaped into a three dimensional object or material as shown in FIG. 2. In FIG. 2, the dissimilar first electrode 201 and second electrode 202 are coupled into a desired hydrophilic polymer base 203 of a hydrogel 200. First electrode 201 and second electrode 202 can be placed within hydrophilic polymer base 203 as needed to accommodate the desired use.

In embodiments, systems and devices disclosed herein can produce a low level electric current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, between about 100 and about 150 micro-amperes, between about 150 and about 200 micro-amperes, between about 200 and about 250 micro-amperes, between about 250 and about 300 micro-amperes, between about 300 and about 350 micro-amperes, between about 350 and about 400 micro-amperes, between about 400 and about 450 micro-amperes, between about 450 and about 500 micro-amperes, between about 500 and about 550 micro-amperes, between about 550 and about 600 micro-amperes, between about 600 and about 650 micro-amperes, between about 650 and about 700 micro-amperes, between about 700 and about 750 micro-amperes, between about 750 and about 800 micro-amperes, between about 800 and about 850 micro-amperes, between about 850 and about 900 micro-amperes, between about 900 and about 950 micro-amperes, between about 950 and about 1000 micro-amperes (1 milli-amp [mA]), between about 1.0 and about 1.1 mA, between about 1.1 and about 1.2 mA, between about 1.2 and about 1.3 mA, between about 1.3 and about 1.4 mA, between about 1.4 and about 1.5 mA, between about 1.5 and about 1.6 mA, between about 1.6 and about 1.7 mA, between about 1.7 and about 1.8 mA, between about 1.8 and about 1.9 mA, between about 1.9 and about 2.0 mA, between about 2.0 and about 2.1 mA, between about 2.1 and about 2.2 mA, between about 2.2 and about 2.3 mA, between about 2.3 and about 2.4 mA, between about 2.4 and about 2.5 mA, between about 2.5 and about 2.6 mA, between about 2.6 and about 2.7 mA, between about 2.7 and about 2.8 mA, between about 2.8 and about 2.9 mA, between about 2.9 and about 3.0 mA, between about 3.0 and about 3.1 mA, between about 3.1 and about 3.2 mA, between about 3.2 and about 3.3 mA, between about 3.3 and about 3.4 mA, between about 3.4 and about 3.5 mA, between about 3.5 and about 3.6 mA, between about 3.6 and about 3.7 mA, between about 3.7 and about 3.8 mA, between about 3.8 and about 3.9 mA, between about 3.9 and about 4.0 mA, between about 4.0 and about 4.1 mA, between about 4.1 and about 4.2 mA, between about 4.2 and about 4.3 mA, between about 4.3 and about 4.4 mA, between about 4.4 and about 4.5 mA, between about 4.5 and about 5.0 mA, between about 5.0 and about 5.5 mA, between about 5.5 and about 6.0 mA, between about 6.0 and about 6.5 mA, between about 6.5 and about 7.0 mA, between about 7.5 and about 8.0 mA, between about 8.0 and about 8.5 mA, between about 8.5 and about 9.0 mA, between about 9.0 and about 9.5 mA, between about 9.5 and about 10.0 mA, between about 10.0 and about 10.5 mA, between about 10.5 and about 11.0 mA, between about 11.0 and about 11.5 mA, between about 11.5 and about 12.0 mA, between about 12.0 and about 12.5 mA, between about 12.5 and about 13.0 mA, between about 13.0 and about 13.5 mA, between about 13.5 and about 14.0 mA, between about 14.0 and about 14.5 mA, between about 14.5 and about 15.0 mA, or the like.

In embodiments, systems and devices disclosed herein can produce a low level electric current of between for example about 1 and about 400 micro-amperes, between about 20 and about 380 micro-amperes, between about 40 and about 360 micro-amperes, between about 60 and about 340 micro-amperes, between about 80 and about 320 micro-amperes, between about 100 and about 3000 micro-amperes, between about 120 and about 280 micro-amperes, between about 140 and about 260 micro-amperes, between about 160 and about 240 micro-amperes, between about 180 and about 220 micro-amperes, or the like.

In embodiments, systems and devices disclosed herein can produce a low level electric current of between for example about 1 micro-ampere and about 1 milli-ampere, between about 50 and about 800 micro-amperes, between about 200 and about 600 micro-amperes, between about 400 and about 500 micro-amperes, or the like.

In embodiments, systems and devices disclosed herein can produce a low level electric current of about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, about 450 micro-amperes, about 500 micro-amperes, about 550 micro-amperes, about 600 micro-amperes, about 650 micro-amperes, about 700 micro-amperes, about 750 micro-amperes, about 800 micro-amperes, about 850 micro-amperes, about 900 micro-amperes, about 950 micro-amperes, about 1 milli-ampere, or the like.

In embodiments, the disclosed systems and devices can produce a low level electric current of not more than about 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, not more than about 500 micro-amperes, not more than about 520 micro-amperes, not more than about 540 micro-amperes, not more than about 560 micro-amperes, not more than about 580 micro-amperes, not more than about 600 micro-amperes, not more than about 620 micro-amperes, not more than about 640 micro-amperes, not more than about 660 micro-amperes, not more than about 680 micro-amperes, not more than about 700 micro-amperes, not more than about 720 micro-amperes, not more than about 740 micro-amperes, not more than about 760 micro-amperes, not more than about 780 micro-amperes, not more than about 800 micro-amperes, not more than about 820 micro-amperes, not more than about 840 micro-amperes, not more than about 860 micro-amperes, not more than about 880 micro-amperes, not more than about 900 micro-amperes, not more than about 920 micro-amperes, not more than about 940 micro-amperes, not more than about 960 micro-amperes, not more than about 980 micro-amperes, or the like.

In embodiments, systems and devices disclosed herein can produce a low level electric current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, not less than about 420 micro-amperes, not less than about 440 micro-amperes, not less than about 460 micro-amperes, not less than about 480 micro-amperes, not less than about 500 micro-amperes, not less than about 520 micro-amperes, not less than about 540 micro-amperes, not less than about 560 micro-amperes, not less than about 580 micro-amperes, not less than about 600 micro-amperes, not less than about 620 micro-amperes, not less than about 640 micro-amperes, not less than about 660 micro-amperes, not less than about 680 micro-amperes, not less than about 700 micro-amperes, not less than about 720 micro-amperes, not less than about 740 micro-amperes, not less than about 760 micro-amperes, not less than about 780 micro-amperes, not less than about 800 micro-amperes, not less than about 820 micro-amperes, not less than about 840 micro-amperes, not less than about 860 micro-amperes, not less than about 880 micro-amperes, not less than about 900 micro-amperes, not less than about 920 micro-amperes, not less than about 940 micro-amperes, not less than about 960 micro-amperes, not less than about 980 micro-amperes, or the like.

To maximize the number of voltaic cells, in various embodiments, a "pattern" (in some hydrogels, the positions of the electrodes can change) of alternating silver masses (e.g., 101 as shown in FIG. 1) or electrodes or reservoirs and zinc masses (e.g., 102 as shown in FIG. 1) or electrodes or reservoirs can create an array of electrical currents across the hydrogel. A basic embodiment, shown in FIG. 1, has each mass of silver randomly spaced from masses of zinc, and has each mass of zinc randomly spaced from masses of silver, according to an embodiment. In another embodiment, mass of silver can be equally spaced from masses of zinc, and has each mass of zinc equally spaced from masses of silver. That is, the electrodes or reservoirs or dots can either be a uniform pattern, a random pattern, or a combination of the like. The first electrode 101 is separated from the second electrode 102 by a hydrophilic polymer base 103. The designs of first electrode 101 and second electrode 102 are simply round dots, and in an embodiment, are repeated throughout the hydrogel. For an exemplary device comprising silver and zinc, each silver design preferably has about twice as much mass as each zinc design, in an embodiment. For the embodiment in FIG. 1, the silver designs are most preferably about a millimeter from each of the closest four zinc designs, and vice-versa. The resulting pattern of dissimilar metal masses defines an array of voltaic cells when introduced to an electrolytic solution.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid such as a cosmetic cream can create approximately 1 volt of potential that will penetrate substantially through a hydrogel and its surrounding surfaces. Closer spacing of the dots can decrease the resistance, providing less potential, and the current will not penetrate as deeply. If the spacing falls below about one tenth of a millimeter, a benefit of the spontaneous reaction is that which is also present with a direct reaction; silver can be electrically driven into the skin. Therefore, spacing between the closest conductive materials can be, for example, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, 91 μm, 92 μm, 93 μm, 94 μm, 95 μm, 96 μm, 97 μm, 98 μm, 99 μm, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials or electrodes or dots can be not more than 0.1 mm, or not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials or electrodes or dots can be not less than 0.1 mm, not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Disclosures of the present specification comprise LLEC or LLEF systems comprising a hydrophilic polymer base and a first electrode design formed from a first conductive liquid that comprises a mixture of a polymer and a first element, the first conductive liquid being applied into a position of contact with the primary surface, the first element comprising a metal species, and the first electrode design comprising at least one dot or reservoir, wherein selective ones of the at least one dot or reservoir have approximately a 1.5 µm+/−1 µm mean diameter; a second electrode design formed from a second conductive liquid that comprises a mixture of a polymer and a second element, the second element comprising a different metal species than the first element, the second conductive liquid being printed into a position of contact with the primary surface, and the second electrode design comprising at least one other dot or reservoir, wherein selective ones of the at least one other dot or reservoir have approximately a 2 µm+/−2 µm mean diameter; a spacing on the primary surface that is between the first electrode design and the second electrode design such that the first electrode design does not physically contact the second electrode design, wherein the spacing is approximately 1.5 µm+/−1 µm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter of 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, 5.0 µm, or the like not exceeding 1 mm.

In further embodiments, electrodes, dots or reservoirs can have a mean diameter of not less than 0.2 µm, or not less than 0.3 µm, not less than 0.4 µm, not less than 0.5 µm, not less than 0.6 µm, not less than 0.7 µm, not less than 0.8 µm, not less than 0.9 µm, not less than 1.0 µm, not less than 1.1 µm, not less than 1.2 µm, not less than 1.3 µm, not less than 1.4 µm, not less than 1.5 µm, not less than 1.6 µm, not less than 1.7 µm, not less than 1.8 µm, not less than 1.9 µm, not less than 2.0 µm, not less than 2.1 µm, not less than 2.2 µm, not less than 2.3 µm, not less than 2.4 µm, not less than 2.5 µm, not less than 2.6 µm, not less than 2.7 µm, not less than 2.8 µm, not less than 2.9 µm, not less than 3.0 µm, not less than 3.1 µm, not less than 3.2 µm, not less than 3.3 µm, not less than 3.4 µm, not less than 3.5 µm, not less than 3.6 µm, not less than 3.7 µm, not less than 3.8 µm, not less than 3.9 µm, not less than 4.0 µm, not less than 4.1 µm, not less than 4.2 µm, not less than 4.3 µm, not less than 4.4 µm, not less than 4.5 µm, not less than 4.6 µm, not less than 4.7 µm, not less than 4.8 µm, not less than 4.9 µm, not less than 5.0 µm, or the like not exceeding 1 mm.

In further embodiments, electrodes, dots or reservoirs can have a mean diameter of not more than 0.2 µm, or not more than 0.3 µm, not more than 0.4 µm, not more than 0.5 µm, not more than 0.6 µm, not more than 0.7 µm, not more than 0.8 µm, not more than 0.9 µm, not more than 1.0 µm, not more than 1.1 µm, not more than 1.2 µm, not more than 1.3 µm, not more than 1.4 µm, not more than 1.5 µm, not more than 1.6 µm, not more than 1.7 µm, not more than 1.8 µm, not more than 1.9 µm, not more than 2.0 µm, not more than 2.1 µm, not more than 2.2 µm, not more than 2.3 µm, not more than 2.4 µm, not more than 2.5 µm, not more than 2.6 µm, not more than 2.7 µm, not more than 2.8 µm, not more than 2.9 µm, not more than 3.0 µm, not more than 3.1 µm, not more than 3.2 µm, not more than 3.3 µm, not more than 3.4 µm, not more than 3.5 µm, not more than 3.6 µm, not more than 3.7 µm, not more than 3.8 µm, not more than 3.9 µm, not more than 4.0 µm, not more than 4.1 µm, not more than 4.2 µm, not more than 4.3 µm, not more than 4.4 µm, not more than 4.5 µm, not more than 4.6 µm, not more than 4.7 µm, not more than 4.8 µm, not more than 4.9 µm, not more than 5.0 µm, or the like.

Disclosures of the present specification include LLEC or LLEF systems comprising a primary surface of a material wherein the material is adapted to be applied to an area of tissue such as a muscle; and a first electrode design formed from a first conductive liquid that includes a mixture of a polymer and a first element, the first conductive liquid being applied into a position of contact with the primary surface, the first element including a metal species, and the first electrode design including at least one dot or reservoir, wherein selective ones of the at least one dot or reservoir have approximately a 1.5 mm+1-1 mm mean diameter.

In embodiments, electrodes, dots or reservoirs can have a mean diameter of 0.2 mm, or 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

In further embodiments, electrodes, dots or reservoirs can have a mean diameter of not less than 0.2 mm, or not less than 0.3 mm, not less than 0.4 mm, not less than 0.5 mm, not less than 0.6 mm, not less than 0.7 mm, not less than 0.8 mm, not less than 0.9 mm, not less than 1.0 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2.0 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3.0 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4.0 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5.0 mm, or the like.

In further embodiments, electrodes, dots or reservoirs can have a mean diameter of not more than 0.2 mm, or not more than 0.3 mm, not more than 0.4 mm, not more than 0.5 mm, not more than 0.6 mm, not more than 0.7 mm, not more than 0.8 mm, not more than 0.9 mm, not more than 1.0 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2.0 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3.0 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4.0 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5.0 mm, or the like.

The material concentrations or quantities within and/or the relative sizes (e.g., dimensions or surface area) of the reservoirs or dots or electrodes can be selected deliberately to achieve various characteristics of the systems' behavior. For example, the quantities of material within a reservoir can be selected to provide an apparatus having an operational behavior that depletes at approximately a desired rate and/or that "dies" after an approximate period of time after activation. In an embodiment the reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material. Further disclosure relating to producing reservoirs that are configured to sustain one or more currents for an approximate pre-determined period of time can be found in U.S. Pat. No. 7,904,147 entitled SUBSTANTIALLY PLANAR ARTICLE AND METHODS OF MANUFACTURE issued Mar. 8, 2011, which is incorporated by reference herein in its entirety.

In various embodiments the difference of the standard potentials of the first and second reservoirs or electrodes or dots can be in a range from about 0.05 V to approximately 5.0 V. For example, the standard potential can be 0.05 V, 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment, the difference between the standard potentials of the first and second reservoirs or electrodes or dots can be at least 0.05 V, at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs or electrodes or dots can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials. Further disclosure relating to standard potentials can be found in U.S. Pat. No. 8,224,439 entitled BATTERIES AND METHODS OF MANUFACTURE AND USE issued Jul. 17, 2012, which is incorporated be reference herein in its entirety.

Figure 3:
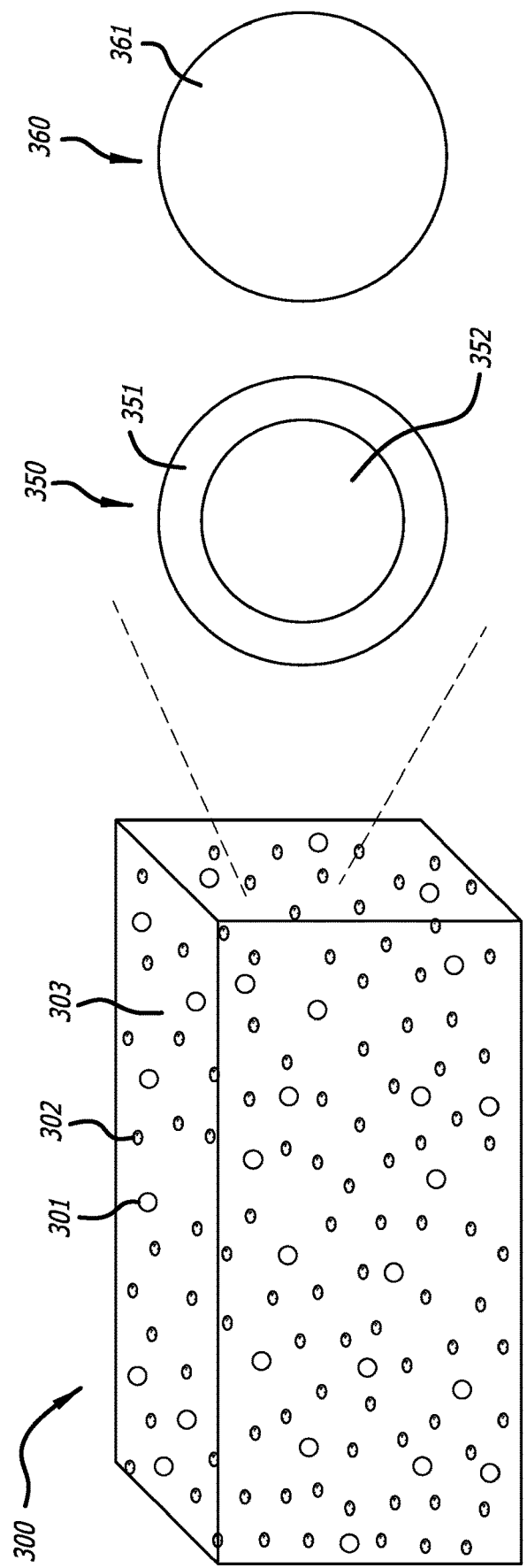
FIG. 3 depicts a graphical representation of the microparticles within a bioelectric hydrogel according to one or more embodiments.

FIG. 3 depicts a graphical representation of a microparticle or microsphere of a bioelectric hydrogel according to one or more embodiments. Hydrogel 300 comprises a dissimilar first electrode 301 and a second electrode 302 that are coupled into a desired hydrophilic polymer base 303 of a hydrogel. Prior to coupling the electrodes or dots to the hydrophilic polymer base, the microspheres can be coated, plated, or printed with a conductive material or ink using a biocompatible binder mixed with each of the dissimilar metals that will create voltaic cells. Most inks are simply a carrier, and a binder mixed with pigment. Similarly, conductive metal solutions can be a binder mixed with a conductive element. The resulting conductive metal solutions can be used with an application method to apply the conductive material to the microspheres in predetermined thickness or depth. For example, microsphere 350 can be coated with a conductive metal 351 while leaving the interior 352 of the microsphere unchanged. In another embodiment, microsphere can be completely formed by a conductive material 361 with no unchanged interior 352 of the microsphere. Once the conductive metal solutions dry and/or cure, the conductive material can substantially maintain their relative position on a microsphere, even in a flexible material such as a hydrogel used for a LLEC or LLEF system. The conductive metal solution applied to the microspheres can be allowed to dry before being applied to a hydrophilic polymer base so that the conductive materials do not mix within a hydrogel, which could interrupt the array and cause direct reactions that will release the elements.

Figure 13:
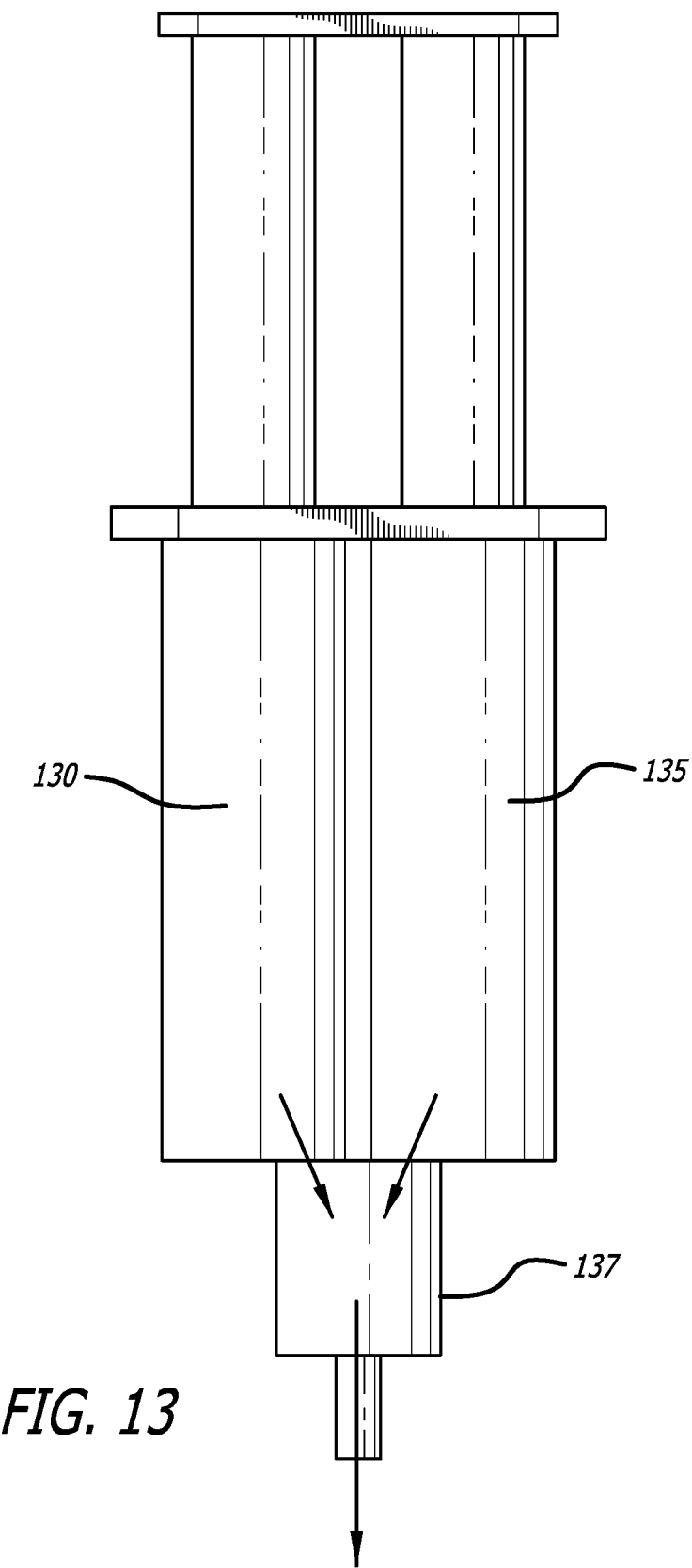
FIG. 13 depicts a two-component system wherein two hydrogels, each containing a separate electrode matrix, are combined upon use.

Embodiments can include systems and devices in the form of a two-component gel that is mixed on use. For example, in embodiments disclosed devices can comprise a first electrode material suspended in a hydrogel, and a second electrode material suspended in a separate hydrogel (in a separate reservoir). The hydrogels can then be mixed on use, thus activating the material. FIG. 13 demonstrates an exemplary embodiment. Reservoir 130 comprising a first electrode material and reservoir 135 comprising a second electrode material are mixed 137 when the material is applied. Upon mixing, the material is activated and produces current.

In certain embodiments, disclosed systems and devices can comprise a first electrode material and a second electrode material in a single gel. The individual electrodes or dots can be isolated, for example with a time, temperature, or pH-dependent membrane or barrier or coating. For example, the membrane can be designed to degrade, thus exposing the electrodes to each other, after a set period of time, or at a desired temperature, or at a desired pH. For example, the membrane can be designed to degrade at body temperature, for example at human body temperature. In embodiments the membrane can be designed to degrade upon mechanical stress, for example upon application. In certain embodiments, for example treatment methods, it can be preferable to utilize AC or DC current. For example, embodiments disclosed herein can employ phased array, pulsed, square wave, sinusoidal, or other wave forms, combinations, or the like. Certain embodiments utilize a controller to produce and control power production and/or distribution to the device.

Embodiments can comprise coatings on the surface or within the hydrogel, such as, for example, over or between the electrodes or cells or an excipient or activation agent suspended within the coating. Coatings can comprise, for example, silicone, and electrolytic mixture, hypoallergenic agents, drugs, biologics, stem cells, skin substitutes, cosmetic products, combinations, or the like. Drugs suitable for use with embodiments of the invention comprise analgesics, antibiotics, anti-inflammatories, or the like.

In embodiments the material can comprise a port to access the interior of the material, for example to add fluid, gel, cosmetic products, a hydrating material, or some other material. Certain embodiments can comprise a "blister" top that can enclose a material such as an antibacterial. In embodiments the blister top can contain a material that is released into or on to the material when the blister is pressed, for example a liquid or cream. For example, embodiments disclosed herein can comprise a blister top containing an antibacterial or the like.

A system or device disclosed herein and placed over tissue such as skin can move relative to the tissue. Reducing the amount of motion between tissue and device can be advantageous to treatment. Slotting or placing cuts into the device can result in less friction or tension on the skin. In embodiments, use of an elastic dressing similar to the elasticity of the skin is also possible.

In embodiments the system comprises a component such as elastic or other such fabric to maintain or help maintain its position. In embodiments the system comprises components such as straps to maintain or help maintain its position. In certain embodiments the system or device comprises a strap on either end of the long axis, or a strap linking on end of the long axis to the other. In embodiments that straps can comprise Velcro or a similar fastening system. In embodiments the straps can comprise elastic materials. In embodiments the hydrogel can be configured into straps as a part of the material.

In further embodiments the strap can comprise a conductive material, for example a wire to electrically link the device with other components, such as monitoring equipment or a power source. In embodiments the device can be wirelessly linked to monitoring or data collection equipment, for example linked via Bluetooth to a cell phone or computer that collects data from the device. In certain embodiments the device can comprise data collection means, such as temperature, pH, pressure, or conductivity data collection means. In certain embodiments, disclosed devices and systems can comprise data collection means, such as temperature, pH, pressure, or conductivity data collection means. Embodiments can comprise a display, for example to visually present, for example, the temperature, pH, pressure, or conductivity data to a user. Embodiments can include, for example, tracking equipment so as to track and/or quantify a user's movements or performance. Embodiments can include, for example, an accelerometer, so as to measure impact forces on a user.

In embodiments the system comprises a component such as an adhesive to maintain or help maintain its position. The adhesive component can be covered with a protective layer that is removed to expose the adhesive at the time of use. In embodiments the adhesive can comprise, for example, sealants, such as hypoallergenic sealants, gecko sealants, mussel sealants, waterproof sealants such as epoxies, and the like. Straps can comprise Velcro or similar materials to aid in maintaining the position of the device.

In embodiments the positioning component can comprise an elastic film with an elasticity, for example, similar to that of skin, or greater than that of skin, or less than that of skin. In embodiments, the LLEC or LLEF system can comprise a laminate where layers of the laminate can be of varying elasticities. For example, an outer layer may be highly elastic and an inner layer in-elastic or less elastic. The in-elastic layer can be made to stretch by placing stress relieving discontinuous regions through the thickness of the material so there is a mechanical displacement rather than stress that would break the hydrogel before stretching would occur. In embodiments the stress relieving discontinuous regions can extend completely through a layer or the system or can be placed where expansion is required. In embodiments of the system the stress relieving discontinuous regions do not extend all the way through the system or a portion of the system such as the substrate. In embodiments the discontinuous regions can pass halfway through the long axis of the substrate.

In certain embodiments, a substrate comprising an array can comprise one layer of a composite dressing, for example a composite garment or fabric comprising the substrate, an adhesive layer, an expandable absorbent layer, and a stretchable, expandable film layer. The expandable absorbent layer can absorb excess fluid from the substrate and expand away from the treatment area, thus preventing oversaturation of the treatment area with resultant maceration and increased infection risk. The stretchable, expandable film layer can stretch to accommodate a larger foam volume as the foam absorbs liquid. This aspect reduces shear forces on the skin. Additionally, the vertically-expanding foam and film allows the dressing to absorb more volume of fluid in a smaller contact area.

In embodiments the device or substrate can be shaped to fit an area of desired use, for example the human face, or around a subject's eyes, or around a subject's forehead, a subject's cheeks, a subject's chin, a subject's back, a subject's chest, a subject's legs, a subject's ankle, a subject's arms, a subject's wound or any area where treatment is desired. For example, in embodiments the device can be shaped to fit an area where an injury has occurred, such as a patient's legs where there are abrasions from a bicycle accident or a patient's arm where tissue is surgically removed to treat a medical condition. In certain embodiments the device can be shaped to fit an area where an injury previously occurred to prevent reoccurrence of the injury. In other embodiments the device can be shaped to fit and area where increased cellular energy is needed such as the quadriceps in ones legs while running.

Embodiments disclosed herein comprise biocompatible electrodes or reservoirs or dots within a hydrogel, for example an ointment, a cell culture medium, or the like. In embodiments the hydrogel can be configured into a variety of shapes, for example to better follow the contours of an area to be treated, such as the face or back. In embodiments the hydrogel can be configured into a gauze or mesh or plastic.

Embodiments disclosed herein can comprise a hydrogel and a substrate. Suitable substrates for use in embodiments disclosed herein can be absorbent or non-absorbent textiles, low-adhesives, vapor permeable films, hydrocolloids, hydrogels, alginates, foams, foam-based materials, cellulose-based materials comprising Kettenbach fibers, hollow tubes, fibrous materials, such as those impregnated with anhydrous/hygroscopic materials, beads and the like, or any suitable material as known in the art. In embodiments the material can form, for example, a mask, such as that worn on the body, a pant, a glove, a sock, a shirt or a portion thereof, for example an elastic or compression shirt, or a portion thereof, a wrapping, towel, cloth, fabric, or the like. In other embodiment the hydrogel can be configured into multi layer embodiments from a variation of the described above.

In embodiments the substrate layer can be non-pliable, for example, a plastic such as a pad (for example a shoulder or thigh pad) or a helmet interior or the like.

A LLEC or LLEF system disclosed herein can comprise "anchor" regions or "arms" or straps to affix the system securely. The anchor regions or arms can anchor the LLEC or LLEF system. For example, a LLEC or LLEF system can be secured to an area proximal to a joint or irregular skin surface, and anchor regions of the system can extend to areas of minimal stress or movement to securely affix the system. Further, the LLEC system can reduce stress on an area, for example by "countering" the physical stress caused by movement.

In embodiments the LLEC or LLEF system can comprise additional materials to aid in treatment.

In embodiments, the LLEC or LLEF system can comprise instructions or directions on how to place the system to maximize its performance. Embodiments comprise a kit comprising an LLEC or LLEF system and directions for its use.

In certain embodiments dissimilar metals can be used to create an electric field with a desired voltage. In certain embodiments the pattern of reservoirs can control the watt density and shape of the electric field.

In certain embodiments dissimilar metals can be used to create an electric field with a desired voltage within the hydrogel. In certain embodiments the pattern of reservoirs can control the watt density and shape of the electric field.

Certain embodiments can utilize a power source to create the electric current, such as a battery or a micro-battery. The power source can be any energy source capable of generating a current in the LLEC system and can comprise, for example, AC power, DC power, radio frequencies (RF) such as pulsed RF, induction, ultrasound, and the like.

Similarly, electrodes or reservoirs or dots can adhere or bond to a substrate through use of a biocompatible binder. Conductive metal solutions can comprise a binder mixed with a conductive element. The resulting conductive metal solution can be used with an application method such as screen printing to apply the electrodes to the primary surface in predetermined patterns. Once the conductive metal solution dries and/or cures, the patterns of spaced electrodes can substantially maintain their relative position, even on a flexible material such as that used for a LLEC or LLEF system. The conductive metal solution can be allowed to dry before being applied to a surface.

In another embodiment, the reservoirs or dots or electrodes are configured to be same specific gravity as the hydrophilic polymer base of the hydrogel. This embodiment, allows the reservoirs or dots to be suspended in the hydrogel for a desired used without the reservoirs or dots being pulled to the bottom of the hydrogels due to other factors such as gravity. In particular, the reservoirs or dots will not settle and the hydrogel can be manufactured and stored for extended periods of time.

In certain embodiments that utilize a poly-cellulose binder, the binder itself can have a beneficial effect such as reducing the local concentration of matrix metallo-proteases through an iontophoretic process that drives the cellulose into the surrounding tissue. This process can be used to electronically drive other components such as drugs into the surrounding tissue.

The binder can comprise any biocompatible liquid material that can be mixed with a conductive element (preferably metallic crystals of silver or zinc) to create a conductive solution which can be applied as a thin coating to a microsphere. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.999%) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution. For better quality control and more consistent results, most of the crystals used should be larger than 325 mesh and smaller than 200 mesh. For example the crystals used should be between 200 mesh and 325 mesh, or between 210 mesh and 310 mesh, between 220 mesh and 300 mesh, between 230 mesh and 290 mesh, between 240 mesh and 280 mesh, between 250 mesh and 270 mesh, between 255 mesh and 265 mesh, or the like.

Other powders of metal can be used to make other conductive metal solutions in the same way as described in other embodiments.

The size of the metal crystals, the availability of the surface to the conductive fluid and the ratio of metal to binder affects the release rate of the metal from the mixture. When COLORCON® polyacrylic ink is used as the binder, about 10 to 40 percent of the mixture should be metal for a long term bandage (for example, one that stays on for about 10 days). In embodiments, the percent of the mixture that should be metal can be 8 percent, 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, a typical system will be effective for longer. For example, for a longer term device, the percent of the mixture that should be metal can be 40 percent, 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For LLEC or LLEF systems comprising a pliable substrate it can be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

The voltage present at the site of treatment or within the hydrogel is typically in the range of millivolts but disclosed embodiments can introduce a much higher voltage, for example near 1 volt when using the 1 mm spacing of dissimilar metals already described. The higher voltage is believed to drive the current deeper into the treatment area or within the hydrogel. In this way the current not only can drive silver and zinc into the treatment if desired for treatment, but the current can also provide a stimulatory current so that the entire surface area can be treated. The higher voltage may also increase antimicrobial effect bacteria and preventing biofilms. The electric field can also have beneficial effects on cell migration, ATP production, and angiogenesis.

Embodiments disclosed herein relating to tissue treatment can also comprise selecting a patient or tissue in need of, or that could benefit by, using a bioelectric hydrogel.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then be applied to a hydrogel to create voltaic cells which will become active when brought into contact with an electrolytic solution.

Certain embodiments comprise LLEC or LLEF systems comprising embodiments designed to be used on irregular, non-planar, or "stretching" surfaces. Embodiments disclosed herein can be used with numerous irregular surfaces of the body, comprising the face, the shoulder, the elbow, the wrist, the finger joints, the hip, the knee, the ankle, the toe joints, decubitus wound, diabetic ulcer etc. Additional embodiments disclosed herein can be used in areas where tissue is prone to movement, for example the eyelid, the ear, the lips, the nose, the shoulders, the back, etc.

In certain embodiments, the hydrogel or substrate can be shaped to fit a particular region of the body such as an arm, leg, ankle, chest, decubitus wound, or diabetic ulcer. Additionally, a hydrogel can be shaped to form objects such as petri dishes, prosthetics, or clothing. In various embodiments the hydrogel can have a low viscosity or a high viscosity while forming to such objects or regions of the body.

Figure 4A:
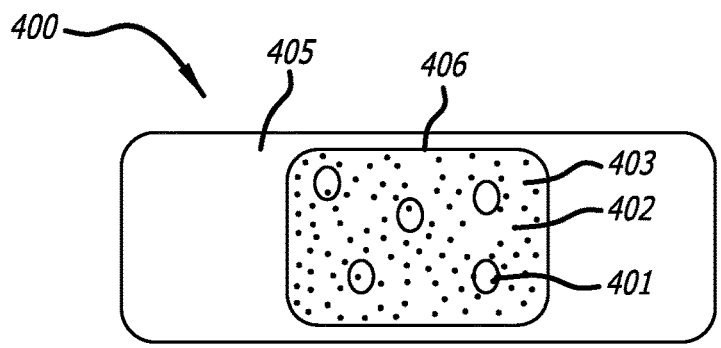
FIGS. 4A-4C depict a alternative graphical representation of a bioelectric hydrogel as a low viscosity material according to one or more embodiments.
Figure 4B:
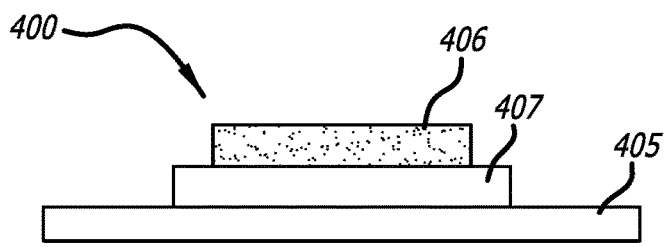
Figure 4C:
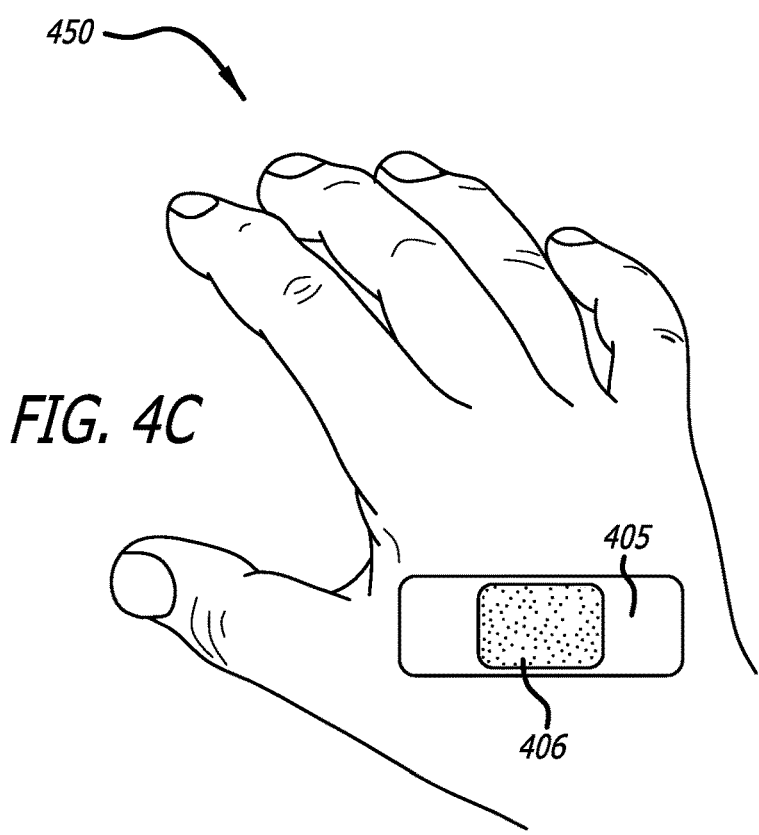

FIGS. 4A-4C depict an alternative graphical representation of a bioelectric hydrogel as a low viscosity material according to one or more embodiments. In FIGS. 4A and 4B, bandage 400 can accommodate a hydrogel with a low viscosity such as an ointment. Bandage 400 comprises affixing element 405 and a dressing element 407. Hydrogel 406 comprises first reservoir or dots 401 and second reservoir or dots 402 coupled to hydrophilic polymer base 403. Hydrogel 406 can be a low viscosity to be applied to dressing element 407 of bandage 400. After application of hydrogel 406, bandage 400 can be then affixed to form to a body part such as hand 450 (as shown in FIG. 4C). In another embodiment, hydrogel 406 can be applied or formed directly to a body part without bandage 400. In another embodiment, hydrogel 406 can also be form to tissue within a wound. In particular, a low viscosity hydrogel can be packed into a wound such a decubitus wound, diabetic ulcer, or the like to directly contact the damaged tissue for treatment or healing. Finally, a hydrogel can be formulated to produce a current and voltage that exactly matched the current of injury produced when an injury of the body occurs.

Figure 5:
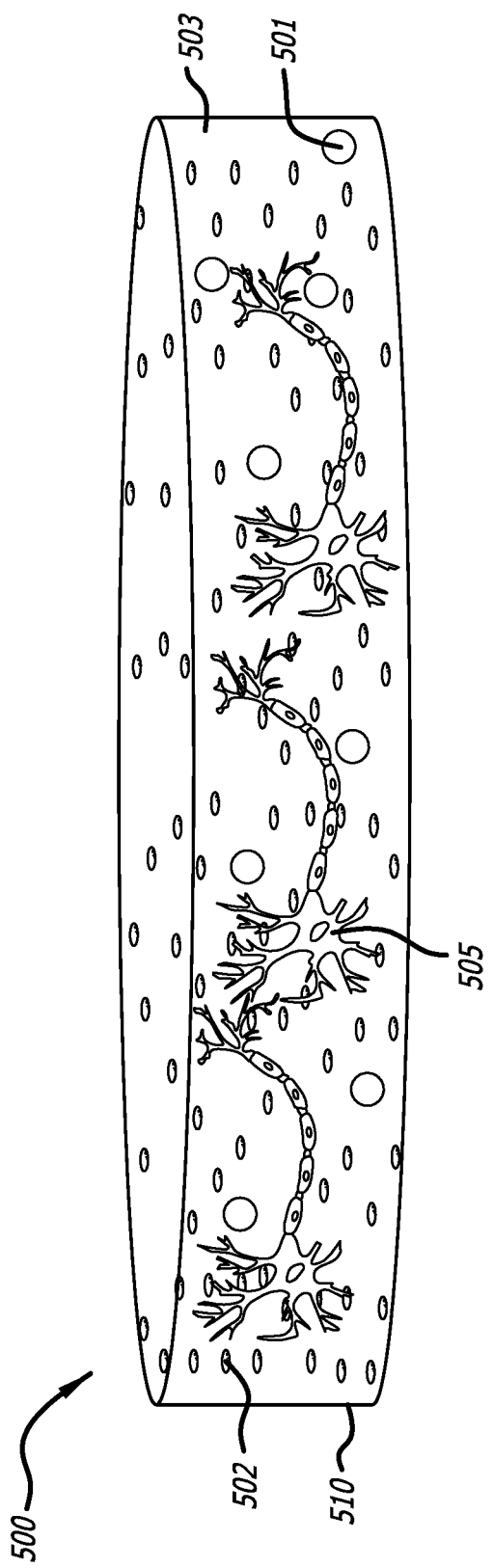
FIG. 5 depicts an alternative graphical representation of a bioelectric hydrogel as a cell culture medium according to one or more embodiments.

FIG. 5 depicts an alternative graphical representation of a bioelectric hydrogel as a cell culture medium according to one or more embodiments. Hydrogels can also be configured as a cellular culture medium. For example, Petri dish 500 can comprise a hydrogel 510 cellular medium. Hydrogel 510 comprises first reservoir or dots 501 and second reservoir or dots 502 coupled to hydrophilic polymer base 503. Hydrogel 510 within Petri dish 500 can be a low viscosity such as a serum free medium or a high viscosity such as an agarose gel. In embodiments the viscosity of hydrogel 510 can be configured to accommodate distinct cellular growth. For example, neuro cells 505 and nerve ganglions are very difficult to grow in vitro. The first reservoir 501 and second reservoir 502 coupled to hydrophilic polymer base 503 in the hydrogel 510 creates a three dimensional energy source which can aid in the cellular culture of neuro cells 505 and nerve ganglions in vitro. In another embodiment, nutrients can be added to hydrogel 510 to facilitate growth and maintain life of neuro cells 505 and nerve ganglions in vitro.

In another embodiment, a hydrogel can be formed or shaped into a Petri dish 500. In particular, hydrogel can be configured to be a high viscosity to be molded into a Petri dish for cellular culture. In this embodiment, electrical stimuli will be directed into the culture medium from the solid structure of the Petri dish.

Figure 6A:
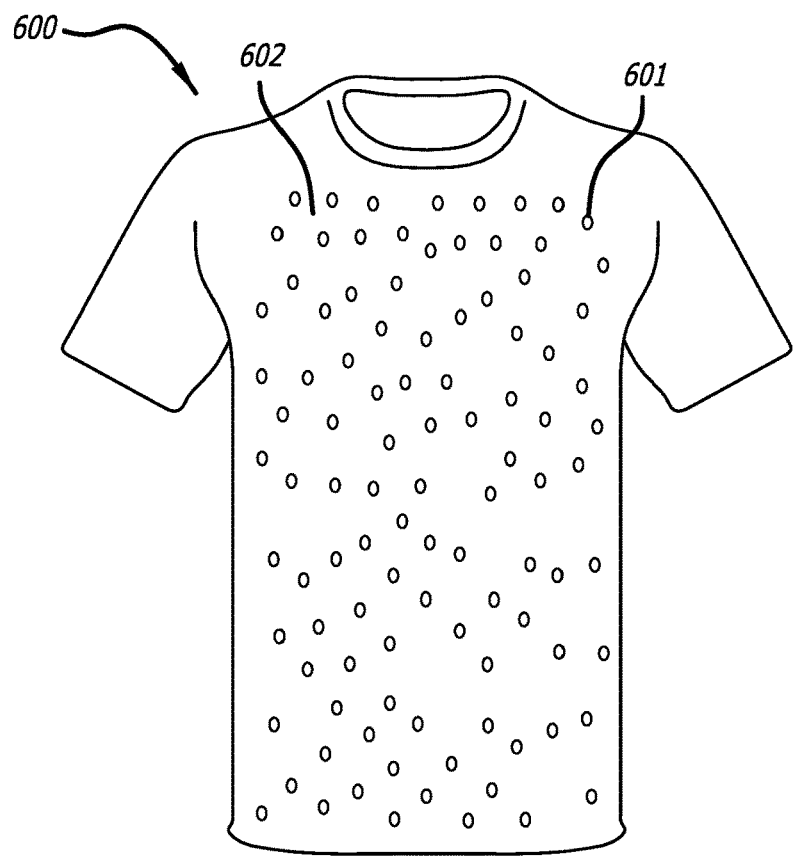
FIG. 6 depicts an alternative graphical representation of a bioelectric hydrogel as a part of a garment.
Figure 6B:
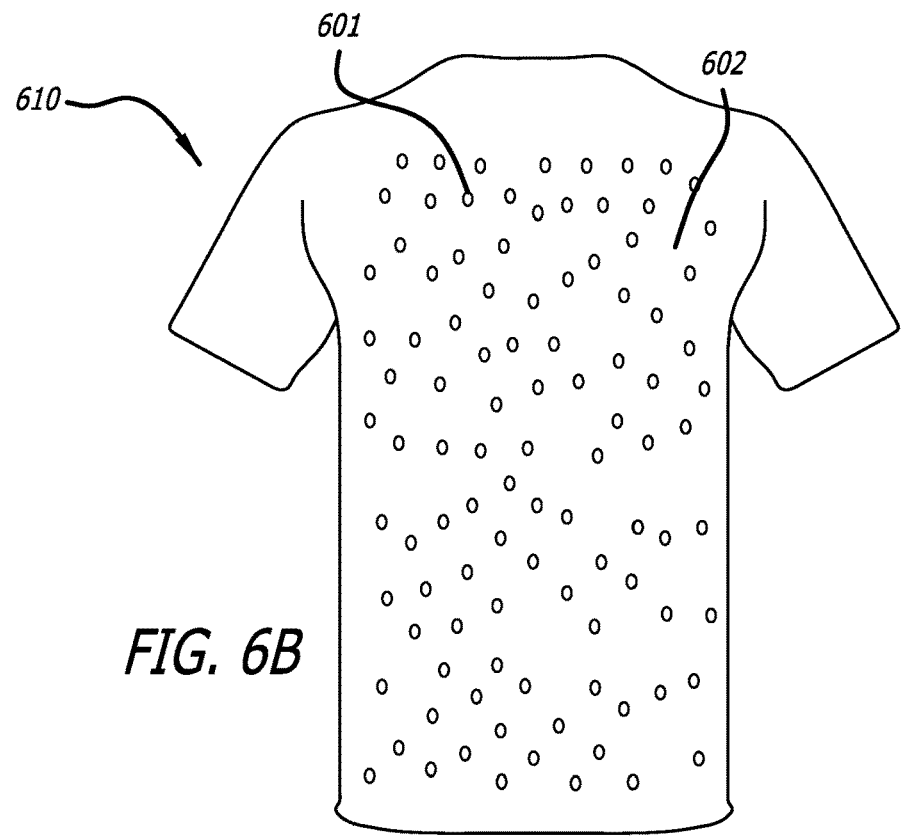

FIG. 6 depicts an alternative graphical representation of a bioelectric hydrogel as a high viscosity material according to one or more embodiments. In FIG. 6, a garment 600 can be shaped or formed from a high viscosity hydrogel. For example, garment 600 can be entirely a solid hydrogel or be woven into hydrogel thread to be used in the manufacturing of such garments. A high viscosity hydrogel also comprises a plurality of reservoirs 601 or dots coupled to a hydrophilic polymer base 602. Reservoirs or dots 601 can provide a LLEF to tissue, when brought in contact with an activating agent, such as sweat. In another embodiment, dots 601 can be configured to a portion of the garment 600 and 610. For example, dots 601 within hydrogel can be applied to only to the lower back of garment 610 to provide LLEF only to the lower back. In certain embodiment, dots 601 within hydrogel can also be removed and a new set of dots 601 can be applied to similar or new location on garment (600 & 610).

Figure 7:
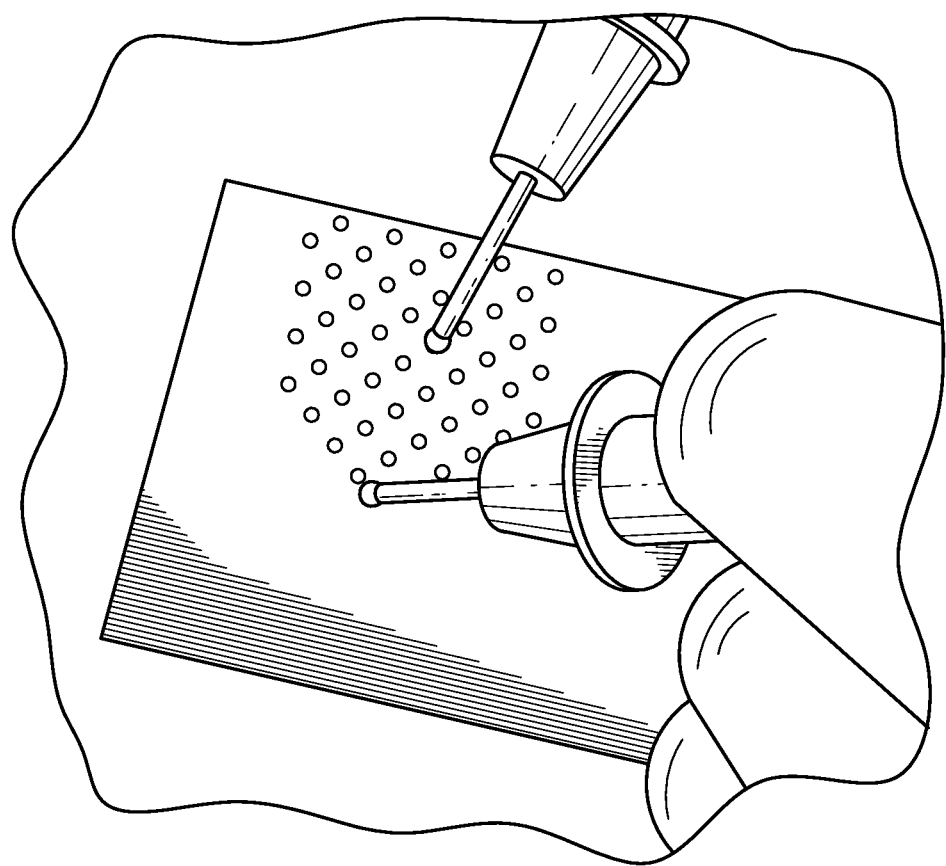
FIG. 7 depicts an embodiment disclosed herein comprising a zinc array embedded on a substrate and a gel comprising a silver array.
Figure 8A:
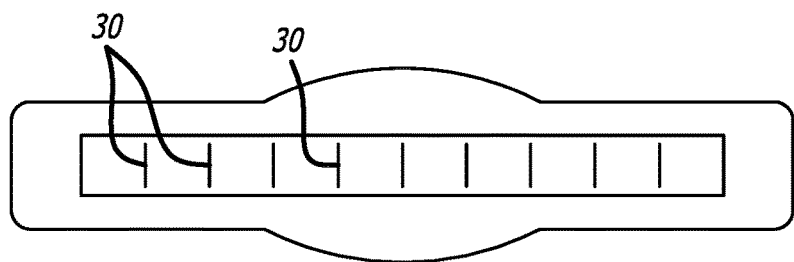
FIGS. 8A-8E depict alternate embodiments showing the location of discontinuous regions as well as anchor regions of the system.
Figure 8B:
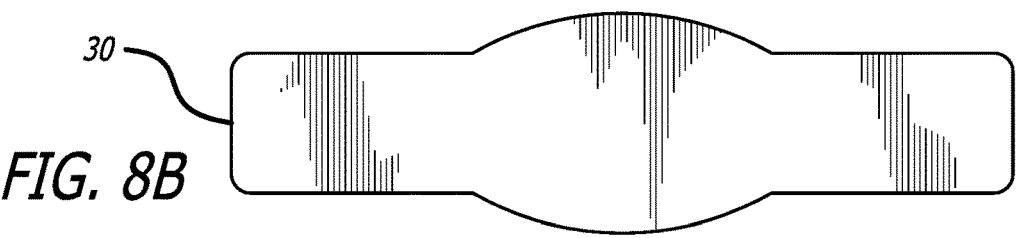
Figure 8C:
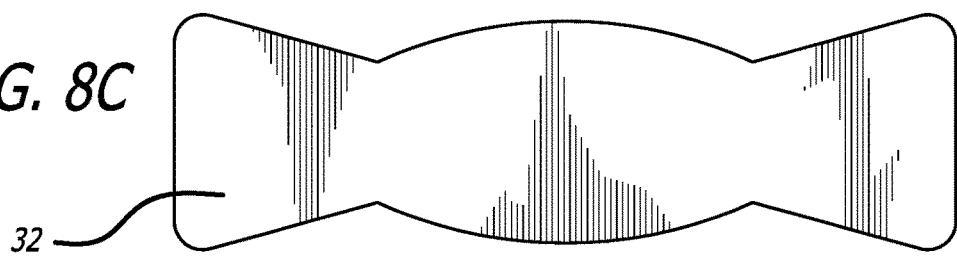
Figure 8D:
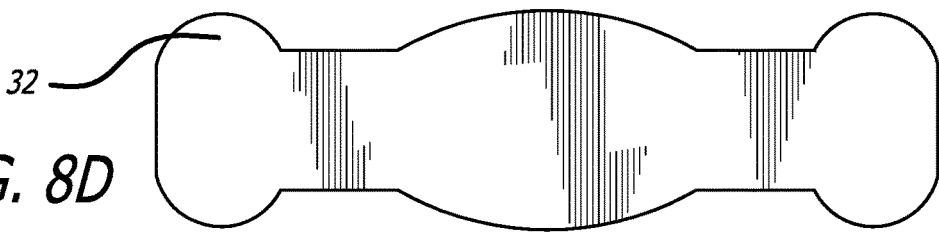
Figure 8E:
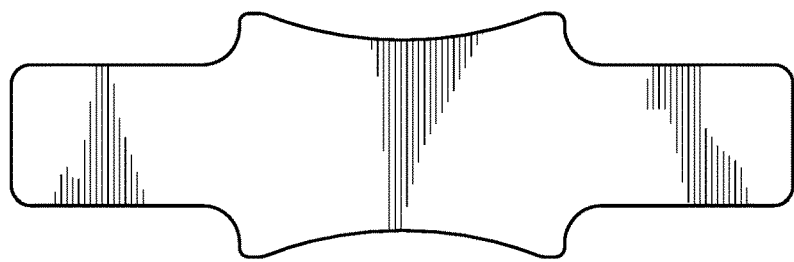

FIG. 7 depicts a multi-phase embodiment utilizing a silver hydrogel phase and a zinc substrate phase.

FIGS. 8A-8E depict alternate embodiments showing the location of discontinuous regions as well as anchor regions of a substrate.

Figure 9A:
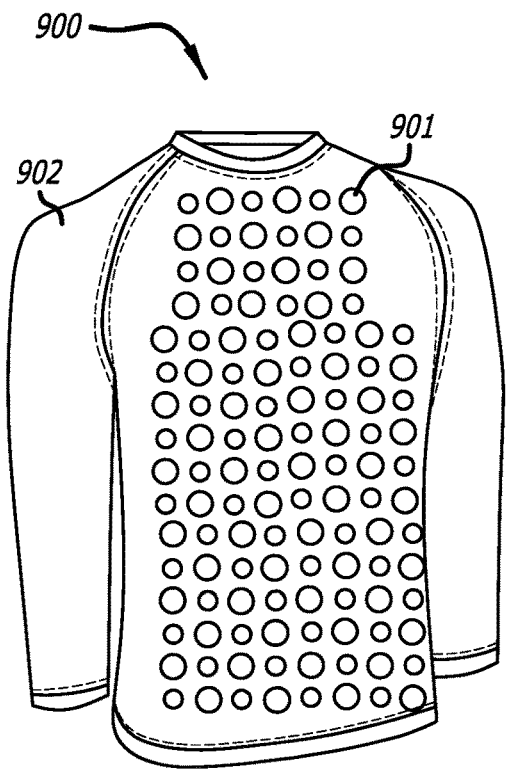
FIGS. 9A-9D depict alternate embodiments showing a garment comprising a multi-array matrix of biocompatible microcells.
Figure 9B:
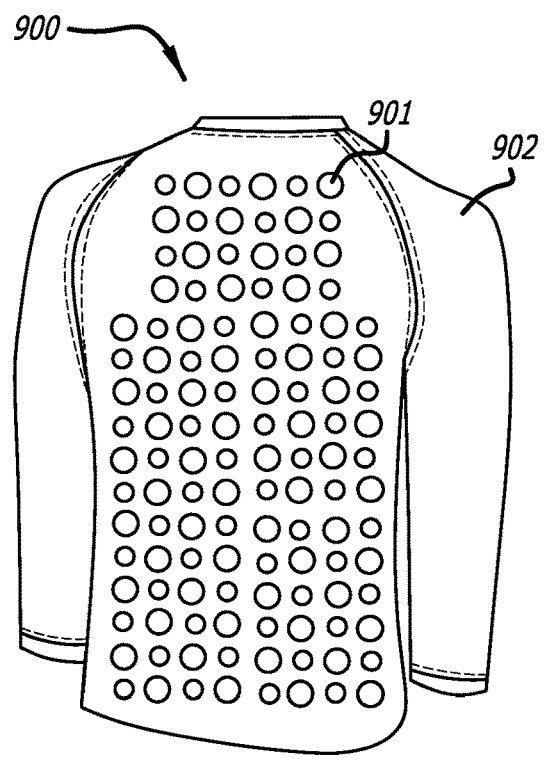
Figure 9C:
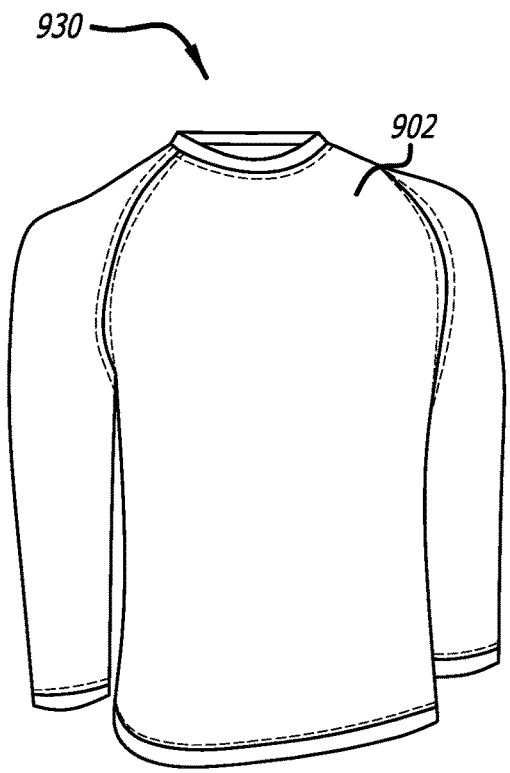
Figure 9D:
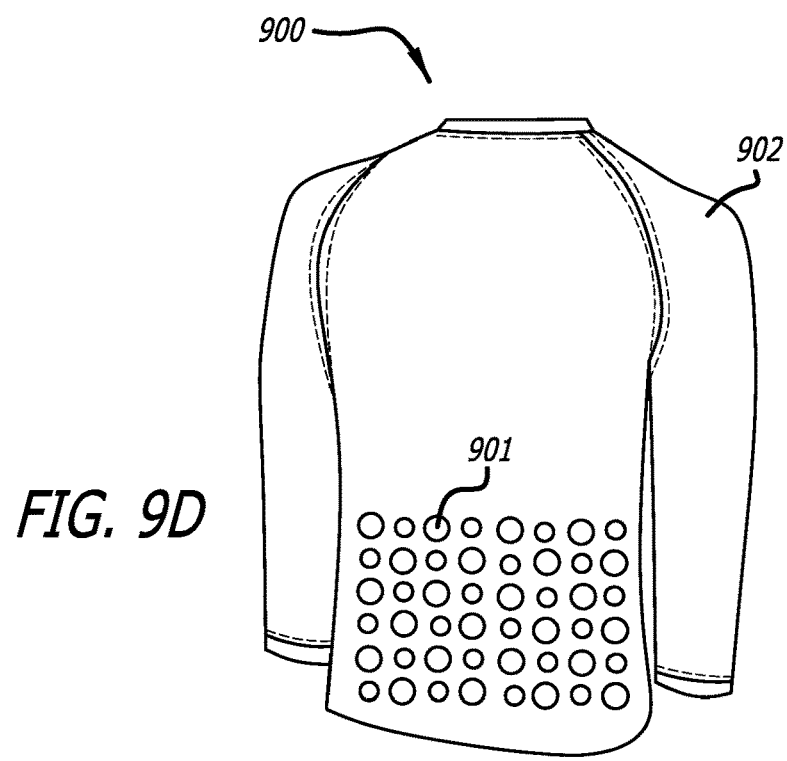

FIGS. 9A-9D depict an example garment 900 comprising a multi-array matrix of biocompatible microcells. Garment 900 comprises electrodes 901 and substrate 902. Electrodes 901 are printed around the entirety of substrate 902 including the back of garment 910. Electrodes 901 can provide a LLEF to tissue, and, when in contact with a conductive material, a LLEC. In another embodiment, electrodes 901 can be printed to a portion of the garment 950, as depicted in FIG. 9B. For example, electrodes 901 can be applied to only the back of garment 960 to provide LLEF to lower back. In certain embodiment, electrodes 901 can also be removed and a new set of dots 901 can be applied to similar or new location on garment (950 & 960). The array can be printed or applied such that it contacts the skin while in use. For example, the array can be printed on or applied to the inside of the garment.

Figure 10:
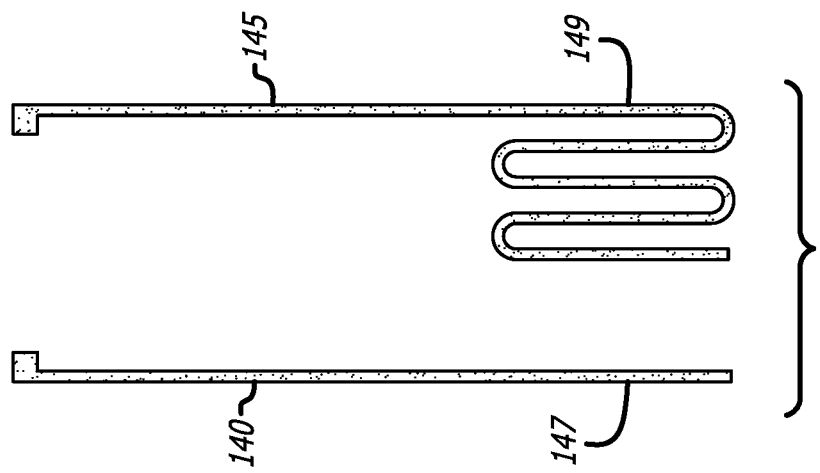
FIG. 10 depicts a detailed plan view of a substrate layer electrode pattern disclosed herein.

FIG. 10 shows an embodiment utilizing two electrodes on a substrate. Upper arms 140 and 145 can be, for example, 1, 2, 3, or 4 mm in width. Lower arm 147 and serpentine 149 can be, for example, 1, 2, 3, or 4 mm in width. The electrodes can be, for example, 1, 2, or 3 mm in depth.

Figure 11:
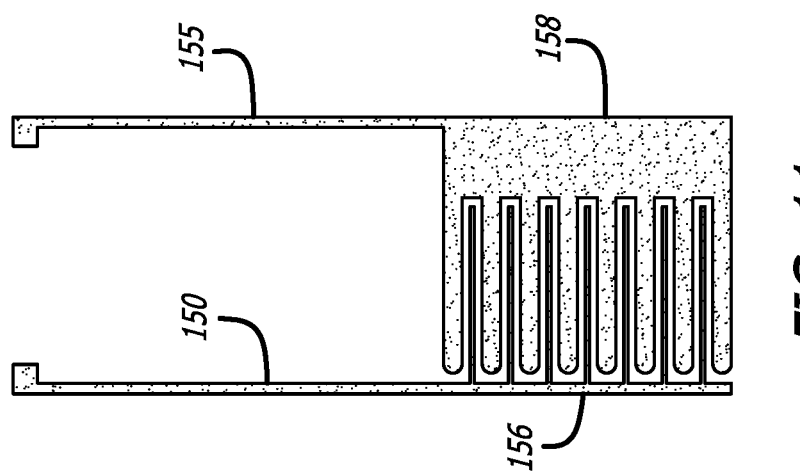
FIG. 11 depicts a detailed plan view of a substrate layer electrode pattern as disclosed herein.

FIG. 11 shows an embodiment utilizing two electrodes on a substrate. Upper arms 150 and 155 can be, for example, 1, 2, 3, or 4 mm in width. The extensions protruding from the lower arm 156 can be, for example, 1, 1.5, 2, 2.5, 3, 3.5, or 4 mm in width. The extensions protruding from the comb 158 can be, for example, 1, 2, 3, 4, 5, 6, or 7 mm in width. The electrodes can be, for example, 1, 2, or 3 mm in depth.

Figure 12:
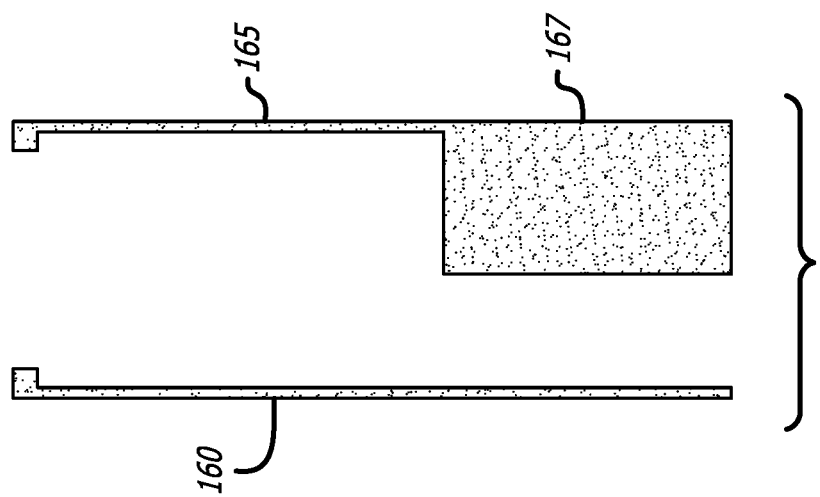
FIG. 12 depicts a detailed plan view of a substrate layer electrode pattern disclosed herein.

FIG. 12 shows an embodiment utilizing two electrodes on a substrate. Upper arms 160 and 165 can be, for example, 1, 2, 3, or 4 mm in width. Lower block 167 can be, for example, 30, 32, 34, 36, 38, 40, 42, 44, 46, 48, 50, 52, or 54 mm along its shorter axis. Lower block 167 can be, for example, 60, 65, 70, 75, 80, 85, 90, 95, or 100 mm along its longer axis. The electrodes can be, for example, 1, 2, or 3 mm in depth.

In embodiments such as those in FIGS. 10-12, the width and depth of the various areas of the electrode can be designed to produce a particular electric field, or, when both electrodes are in contact with a conductive material, a particular electric current. For example, the width of the various areas of the electrode can be, for example, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or 7 mm, or 8 mm, or 9 mm, or 10 mm, or 11 mm, or the like.

In embodiments, the depth or thickness of the various areas of the electrode can be, for example, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

The shortest distance between the two electrodes in an embodiment can be, for example, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, or the like.

In embodiments, the length of the long axis of the electrode can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, 150 mm, 200 mm, 250 mm, 300 mm, 350 mm, 400 mm, 450 mm, 500 mm, 600 mm, 700 mm, 800 mm, 900 mm, 1000 mm, or more, or the like.

In embodiments, the length of the short axis of the electrode can be, for example, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 75 mm, 100 mm, or more, or the like.

Certain embodiments disclosed herein comprise a method of manufacturing a hydrogel LLEC or LLEF system, the method comprising coupling a hydrophilic polymer base with one or more biocompatible electrodes configured to generate at least one of a low level electric field (LLEF) or low level electric current (LLEC). In another embodiment, the method comprises joining with a hydrophilic polymer base with one or more biocompatible electrodes comprising a first bioelectric element comprising a first microparticle formed from a first conductive material, and a second bioelectric element comprising a second microparticle formed from a second conductive material. First microparticle formed from a first conductive material is a reducing agent. Second microparticle formed from a second conductive material is an oxidizing agent. In embodiments the hydrogel can be configured to be a low or high viscosity.

Embodiments disclosed herein comprise LLEC and LLEF systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated.

LLEC/LLEF Systems, Devices, and Methods of Use

Embodiments disclosed herein include LLEC and LLEF systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated. Further disclosure relating to materials that can produce an electrical stimulus can be found in U.S. Pat. No. 7,662,176 entitled FOOTWEAR APPARATUS AND METHODS OF MANUFACTURE AND USE issued Feb. 16, 2010, which is incorporated herein by reference in its entirety.

Treatment of Wounds

The wound healing process includes several phases, including an inflammatory phase and a proliferative phase. The proliferative phase involves cell migration (such as by human keratinocytes) wherein cells migrate into the wound site and cell proliferation wherein the cells reproduce. This phase also involves angiogenesis and the growth of granulation tissue. During cell migration, many epithelial cells have the ability to detect electric fields and respond with directed migration. Their response typically requires $Ca^{2+}$ influx, the presence of specific growth factors such as Integrin and intracellular kinase activity. Most types of cells migrate directionally in a small electric field, a phenomenon called galvanotaxis or electrotaxis. Electric fields of strength equal to those detected at wound edges direct cell migration and can override some other well-accepted coexistent guidance cues such as contact inhibition. Aspects of the present specification disclose in part a method of treating an individual with a wound. Treating a wound can include covering the wound with a LLMC or LLEF system. Embodiments disclosed herein can promote wound healing by directing cell migration during the wound healing process.

In embodiments a wound can be an acute or chronic wound, a diabetic wound of the lower extremities, such as of the legs or feet, a post-radiation tissue injury, crush injuries or compartment syndrome and other acute traumatic ischemic wounds, venous stasis or arterial-insufficiency ulcers, compromised grafts and flaps, infected wounds, pressure ulcers, necrotizing soft-tissue infections, burns, cancer-related wounds, osteomyelitis, surgical wounds, traumatic wounds, insect bites, and the like. In an embodiment a wound can be a non-penetrating wound, such as the result of blunt trauma or friction with other surfaces. Typically this type of wound does not break through the skin and may include an abrasion (scraping of the outer skin layer), a laceration (a tear-like wound), a contusion (swollen bruises due to accumulation of blood and dead cells under skin), or the like. In other embodiments a wound can be a penetrating wound. These result from trauma that breaks through the full thickness of skin and include stab wounds (trauma from sharp objects, such as knives), skin cuts, surgical wounds (intentional cuts in the skin to perform surgical procedures), shrapnel wounds (wounds resulting from exploding shells), or gunshot wounds (wounds resulting from firearms). In further embodiments a wound can be a thermal wound such as resulting from heat or cold, a chemical wound such as resulting from an acid or base, an electrical wound, or the like.

Chronic wounds often do not heal in normal stages, and the wounds can also fail to heal in a timely fashion. LLMC and LLEF systems disclosed herein can promote the healing of chronic wounds by increasing cell migration, cell proliferation, and/or cell signaling. Increased migration can be seen in various cell types, such as for example keratinocytes.

In embodiments, treating the wound can comprise applying a LLMC or LLEF system to the wound such that the system can stretch with movement of the wound and surrounding area. In certain embodiments, the system can be stretched before application to the wound such that the wound management system "pulls" the wound edges together.

In embodiments, methods for treating or dressing a wound comprises the step of topically administering an additional material on the wound surface or upon the matrix of biocompatible microcells. These additional materials can comprise, for example, activation gels, rhPDGF (REGRANEX®), Vibronectin:IGF complexes, CELLSPRAY®, RECELL®, INTEGRA® dermal regeneration template, BIOMEND®, INFUSE®, ALLODERM®, CYMETRA®, SEPRAPACK®, SEPRAMESH®, SKINTEMP®, MEDFIL®, COSMODERM®, COSMOPLAST®, OP-1®, ISOLAGEN®, CARTICEL®, APLIGRAF®, DERMAGRAFT®, TRANSCYTE®, ORCEL®, EPICEL®, and the like. In embodiments the activation gel can be, for example, TEGADERM® 91110 by 3M, Molnlycke Normlgel 0.9% Sodium chloride, HISPAGEL®, LUBRIGEL®, or other compositions useful for maintaining a moist environment about the wound or useful for healing a wound via another mechanism.

Aspects of the present specification provide, in part, methods of reducing a symptom associated with a wound. In an aspect of this embodiment the symptom reduced is edema, hyperemia, erythema, bruising, tenderness, stiffness, swollenness, fever, a chill, a breathing problem, fluid retention, a blood clot, a loss of appetite, an increased heart rate, a formation of granulomas, fibrinous, pus, or non-viscous serous fluid, a formation of an ulcer, or pain.

Treating a wound can refer to reducing the size of, or preventing an increase in size of a wound. For example, treating can reduce the width of a wound by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

Treating a wound can refer to reducing the depth of, or preventing an increase in depth of a wound. For example, treating can reduce the depth of a wound by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

Treatment of Bites

Systems disclosed herein can be used to treat animal bites, for example snake bites. A LLMC or LLEF system can be applied to the bite(s) or bitten area, wherein the low level micro-current or electric field can neutralize the immune reaction to the bites or the venom, or neutralize the antigens present in such bites and thus reduce pain and itching. In embodiments the systems and devices disclosed herein can treat venomous bites by altering the function of venoms, such as, for example, protein-based venoms.

Systems disclosed herein can be used to treat insect bites, for example mosquito bites. A LLMC or LLEF system can be applied to the bite(s) or bitten area, wherein the low level micro-current or electric field can neutralize the immune reaction to the bites or any venom and thus reduce pain and itching.

Treatment of Microbial Infection

Embodiments of the disclosed LLMC and LLEF systems can provide microbicidal activity. For example, embodiments disclosed herein can prevent, limit, or reduce formation of biofilms by interfering with bacterial signaling. Further embodiments can kill bacteria through an established biofilm.

Aspects disclosed herein include systems, devices, and methods for treating parasitic infections. For example, methods disclosed herein include treatments for ectoparasitic infections caused by, for example, *Sarcoptes scabiei* (causes scabies), *Pediculus humanus capitis* (causes head lice), *Phthirus pubis* (causes pubic lice), *Leishmania* (causes leishmaniasis), and the like. Leishmaniasis is a highly focal disease with widely scattered foci. The parasite may survive for decades in asymptomatic infected people, who are of great importance for the transmission since they can spread visceral leishmaniasis indirectly through the sandflies. The parasites can also be transmitted directly from person to person through the sharing of infected needles which is often the case with the *Leishmania*/HIV co-infection. Cutaneous leishmaniasis is the most common form, which causes a sore at the bite site, which heals in a few months to a year, leaving an unpleasant-looking scar. Systems disclosed herein can be used to treat cutaneous leishmaniasis in the initial infection stage as well as the latent stage or in the active disfiguring lesions resulting from the infection.

Cellular Activation

Embodiments of the disclosed LLMC and LLEF systems can increase cell migration by applying an electric current or electric field or both to a treatment area. For example, the systems can increase migration of human keratinocytes. The systems can also be used to promote re-epithelialization for example in a wound.

Embodiments of the disclosed LLMC and LLEF systems can increase glucose uptake in target tissues and cells, for example by applying a LLEF system disclosed herein to a treatment area where increased uptake of glucose is desired. In embodiments glucose uptake can be increased to energize mitochondria.

Embodiments of the disclosed LLMC and LLEF systems can increase cell signaling in target tissues and cells, for example by applying a LLEF system disclosed herein to a treatment area where increased cell signaling is desired.

Embodiments of the disclosed LLMC and LLEF systems can create hydrogen peroxide in target tissues and cells, for example by applying a LLEF system disclosed herein to a treatment area where hydrogen peroxide production is desired.

Treatment of Disease

Embodiments of the disclosed LLMC and LLEF systems can be used to treat disease. For example, embodiments can be used to increase glucose uptake thus reducing serum glucose levels and treating diseases relating to increased glucose levels, such as diabetes. Increasing cellular uptake of glucose can also have a limiting effect on glucose level variations (excursions), thus treating both hyper- and hypoglycemia. In embodiments, methods of treating glucose-related diseases can comprise applying systems of the invention to a patient in need thereof. For example, LLEF or LLMC systems can be applied to a patient's skin, or applied using a catheter, or applied using a pharmaceutical composition. A pharmaceutical composition disclosed herein can be administered to an individual using a variety of routes. Routes of administration suitable for use as disclosed herein include both local and systemic administration. Local administration results in significantly more delivery of a composition to a specific location as compared to the entire body of the individual, whereas, systemic administration results in delivery of a composition to essentially the entire body of the individual.

Further, embodiments disclosed herein can direct cell migration.

Further embodiments can increase cellular protein sulfhydryl levels and cellular glucose uptake. Increased glucose uptake can result in greater mitochondrial activity and thus increased glucose utilization.

Muscle Regeneration

Embodiments of the disclosed LLMC and LLEF systems can be used to regenerate muscle tissue. For example, embodiments can be used to direct macrophage migration to damaged or wounded muscle thus helping to regenerate the muscle.

Disclosed embodiments reduce or prevent muscle damage (for example such as can occur during a workout), for example by activating enzymes that aid in the muscle recovery process, increasing glucose uptake, driving redox signaling, increasing $H_2O_2$ production, increasing cellular protein sulfhydryl levels, and increasing (IGF)-1 R phosphorylation.

Disclosed embodiments can improve muscle recovery, for example by activating enzymes that aid in the muscle recovery process, increasing glucose uptake, driving redox signaling, increasing $H_2O_2$ production, increasing cellular protein sulfhydryl levels, and increasing (IGF)-1 R phosphorylation. Disclosed embodiments can improve muscle function, for example by activating enzymes, increasing glucose uptake, driving redox signaling, increasing $H_2O_2$ production, increasing cellular protein sulfhydryl levels, and increasing (IGF)-1 R phosphorylation. Disclosed embodiments can improve athletic performance, for example by activating enzymes, increasing glucose uptake, driving redox signaling, increasing $H_2O_2$ production, increasing cellular protein sulfhydryl levels, and increasing (IGF)-1 R phosphorylation.

Embodiments disclosed herein include LLEC and LLEF systems that can promote and/or accelerate the muscle recovery process and optimize muscle performance. For example, muscles work when calcium ions are released, which trigger muscle cells to contract. Proteins called actin and myosin form filaments, which form cross-bridges during contraction. The actin and myosin filaments pull past each other when a flood of calcium ions signals contraction, and this causes the muscle sheath to become shorter. This leads all the sheaths (called "sarcomeres") to shorten, and the contraction is synchronized across the entire muscle. The contracting muscles pull on tendons, which in turn pull on the bones to which they are attached. All muscle contractions are triggered by electrical impulses which travel from the brain to the nerve endings in contact with the actin and myosin filaments. Embodiments disclosed herein can increase intracellular calcium levels.

Disclosed embodiments can accelerate muscle recover by, for example, reducing or preventing lactic acidosis, for example by increasing cellular excitation and/or mobilization, and increasing energy production.

Methods disclosed herein can include applying a disclosed embodiment to an area to be treated. Embodiments can include selecting or identifying a patient in need of treatment. In embodiments, methods disclosed herein can include application of a device disclosed herein to an area to be treated.

In embodiments, disclosed methods include application to the treatment area or the device of an antibacterial. In embodiments the antibacterial can be, for example, alcohols, aldehydes, halogen-releasing compounds, peroxides, anilides, biguanides, bisphenols, halophenols, heavy metals, phenols and cresols, quaternary ammonium compounds, and the like. In embodiments the antibacterial agent can comprise, for example, ethanol, isopropanol, glutaraldehyde, formaldehyde, chlorine compounds, iodine compounds, hydrogen peroxide, ozone, peracetic acid, formaldehyde, ethylene oxide, triclocarban, chlorhexidine, alexidine, polymeric biguanides, triclosan, hexachlorophene, PCMX (p-chloro-m-xylenol), silver compounds, mercury compounds, phenol, cresol, cetrimide, benzalkonium chloride, cetylpyridinium chloride, ceftolozane/tazobactam, ceftazidime/avibactam, ceftaroline/avibactam, imipenem/MK-7655, plazomicin, eravacycline, brilacidin, and the like.

In embodiments, compounds that modify resistance to common antibacterials can be employed. For example, some resistance-modifying agents may inhibit multidrug resistance mechanisms, such as drug efflux from the cell, thus increasing the susceptibility of bacteria to an antibacterial. In embodiments, these compounds can include Phe-Arg-β-naphthylamide, or β-lactamase inhibitors such as clavulanic acid and sulbactam.

In embodiments, the system can also be used for preventative treatment of tissue injuries. Preventative treatment can include preventing the reoccurrence of previous muscle injuries. For example, a garment can be shaped to fit a patient's shoulder to prevent recurrence of a deltoid injury.

EXAMPLES

The following non-limiting examples are provided for illustrative purposes only in order to facilitate a more complete understanding of representative embodiments. These examples should not be construed to limit any of the embodiments described in the present specification.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch.

Human keratinocytes were plated under plated under placebo or a LLEC system. Cells were also plated under silver-only or zinc-only dressings. After 24 hours, the scratch assay was performed. Cells plated under the LLEC system displayed increased migration into the "scratched" area as compared to any of the zinc, silver, or placebo dressings. After 9 hours, the cells plated under the LLEC system had almost "closed" the scratch. This demonstrates the importance of electrical activity to cell migration and infiltration.

In addition to the scratch test, genetic expression was tested. Increased insulin growth factor (IGF)-1 R phosphorylation was demonstrated by the cells plated under the LLEC system as compared to cells plated under insulin growth factor alone.

Integrin accumulation also affects cell migration. An increase in integrin accumulation was achieved with the LLEC system. Integrin is necessary for cell migration, and is found on the leading edge of migrating cell.

Thus, the tested LLEC system enhanced cellular migration and IGF-1 R/integrin involvement. This involvement demonstrates the effect that the LLEC system had upon cell receptors involved with the wound healing process.

Example 2

Wound Care Study

The medical histories of patients who received "standard-of-care" wound treatment ("SOC"; n=20), or treatment with a LLEC device as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 μA.

Wounds were assessed until closed or healed. The number of days to wound closure and the rate of wound volume reduction were compared. Patients treated with LLEC received one application of the device each week, or more frequently in the presence of excessive wound exudate, in conjunction with appropriate wound care management. The LLEC was kept moist by saturating with normal saline or conductive hydrogel. Adjunctive therapies (such as negative pressure wound therapy [NPWT], etc.) were administered with SOC or with the use of LLEC unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, comprising diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with lower incidence of increased wound dimensions during the course of healing.

Example 3

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1 R was directly implicated in cell migration. The LLEC also increased keratinocyte mitochondrial membrane potential.

The LLEC was made of polyester printed with dissimilar elemental metals. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with a LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential (Am). Fluorescent dyes JC-1 and TMRM were used to measure mitochondrial membrane potential. JC-1 is a lipophilic dye which produces a red fluorescence with high Am and green fluorescence when Am is low. TMRM produces a red fluorescence proportional to Am. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1 R phosphorylation. Sandwich ELISA using an antibody against phospho-IGF-1 R and total IGF-1 R verified this determination. As observed with the RTK array screening, potent induction in phosphorylation of IGF-1 R was observed 3 h post scratch under the influence of LLEC. IGF-1 R inhibitor attenuated the increased keratinocyte migration observed with LLEC treatment.

MBB (monobromobimane) alkylates thiol groups, displacing the bromine and adding a fluoresce nt tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit alpha-v. There is evidence that integrin, a major extracellular matrix receptor, polarizes in response to applied ES and thus controls directional cell migration. It may be noted that there are a number of integrin subunits, however we chose integrin aV because of evidence of association of alpha-v integrin with IGF-1 R, modulation of IGF-1 receptor signaling, and of driving keratinocyte locomotion. Additionally, integrin alpha v has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1 R mediated keratinocyte migration are a5 integrin and a6 integrin.

Materials and Methods

Cell culture—Immortalized HaCaT human keratinocytes were grown in Dulbecco's low-glucose modified Eagle's medium (Life Technologies, Gaithersburg, Md., U.S.A.) supplemented with 10% fetal bovine serum, 100 U/ml penicillin, and 100 µg/ml streptomycin. The cells were maintained in a standard culture incubator with humidified air containing 5% C02 at 37° C.

Scratch assay—A cell migration assay was performed using culture inserts (IBIDI®, Verona, Wis.) according to the manufacturers instructions. Cell migration was measured using time-lapse phase-contrast microscopy following withdrawal of the insert. Images were analyzed using the Axio-Vision Rel 4.8 software.

N-Acetyl Cysteine Treatment—Cells were pretreated with 5 mM of the thiol antioxidant N-acetylcysteine (Sigma) for 1 h before start of the scratch assay.

IGF-1 R inhibition—When applicable, cells were preincubated with 50 nM IGF-1 R inhibitor, picropodophyllin (Calbiochem, Mass.) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 µl of media. Subsequently, 750 µl of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1 R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturers instructions for flow cytometry.

Integrin alpha V Expression—Human HaCaT cells were grown under the MCD or placebo and harvested 6 h after removing the IBIDI® insert. Staining was done using antibody against integrin aV (Abcam, Cambridge, Mass.).

Example 4

Generation of Superoxide

A LLEC system was tested to determine the effects on superoxide levels which can activate signal pathways. LLEC system increased cellular protein sulfhydryl levels. Further, the LLEC system increased cellular glucose uptake in human keratinocytes. Increased glucose uptake can result in greater mitochondrial activity and thus increased glucose utilization, providing more energy for cellular migration and proliferation. This can "prime" the wound healing process before a surgical incision is made and thus speed incision healing.

Example 5

Effect on *Propionibacterium acnes*

Bacterial Strains and Culture

The main bacterial strain used in this study is *Propionibacterium acnes* and multiple antibiotics-resistant *P. acnes* isolates are to be evaluated.

ATCC medium (7 *Actinomyces* broth) (BD) and/or ATCC medium (593 chopped meat medium) is used for culturing *P. acnes* under an anaerobic condition at 37° C. All experiments are performed under anaerobic conditions.

Culture

LNA (Leeming-Notman agar) medium is prepared and cultured at 34° C. for 14 days.

Planktonic Cells

*P. acnes* is a relatively slow-growing, typically aero-tolerant anaerobic, Gram-positive bacterium (rod). *P. acnes* is cultured under anaerobic condition to determine for efficacy of an embodiment disclosed herein (LLEC system). Overnight bacterial cultures are diluted with fresh culture medium supplemented with 0.1% sodium thioglycolate in PBS to $10^5$ colony forming units (CFUs). Next, the bacterial suspensions (0.5 mL of about 105) are applied directly on LLEC system (2"×2") and control fabrics in Petri-dishes under anaerobic conditions. After 0 h and 24 h post treatments at 37° C., portions of the sample fabrics are placed into anaerobic diluents and vigorously shaken by vortexing for 2 min. The suspensions are diluted serially and plated onto anaerobic plates under an anaerobic condition. After 24 h incubation, the surviving colonies are counted. The LLEC limits bacterial proliferation.

Example 6

Metallic Gel Solution and Single-Metal Substrate

This study demonstrated an alternative method of producing a Redox reaction voltage between two metals (such as zinc and silver), without having both metals embedded in the same substrate. By removing one of the metals from the substrate and mixing it with a conductive gel, the voltage potential was comparable to the voltage potential of both metals embedded in the substrate (PROCELLERA®).

Observed Voltage Potential

|  | Zinc only Substrate | Silver only Substrate |
| --- | --- | --- |
| Silver Gel Solution | ≤.75 V | n/a |
| Zinc Gel Solution | n/a | ≤.85 V |
| Pure Gel Solution | ≤.45 V | ≤.25 V |

*Gel used was sterile AquaSonic 100 by Parker Labs

Example 7

Pre-Treatment and Post-Treatment of Surgical Procedures

Prior to surgery the patient can apply or wear a LLEC system hydrogel over the surgical site, such as the upper arm or bicep area. Surgical procedures can comprise procedures used to treat tenotomy, subpec biceps tenodesis, or rotor cuff repair. The hydrogel consists of an integrated layer of a standard LLEC system. Prior to applying or wearing hydrogel device an activating agent may be applied. The viscosity of the hydrogel provides an intimate contact between the electrodes within the hydrogel device and the skin with minimal movement.

The hydrogel with integrated LLEC system can be applied or worn for 24 hours prior to surgery to initiate incision-healing process by; 1) reducing or eliminating microorganism presence around the incision site; 2) increasing integrin accumulation; 3) increasing cellular protein sulfhydryl levels; 4) increasing $H_2O_2$ production; and 5) up-regulating the TCA (tricarboxylic acid) cycle.

The same LLEC hydrogel device and method can also be applied to a patient's surgical site post-surgery for accelerated healing or treatment.

Example 8

Availability of Cellular Energy and Lactate Threshold

The lactate threshold, also known as lactate inflection point or anaerobic threshold, is the exercise intensity at which lactate (more specifically, lactic acid) starts to accumulate in the blood stream. The reason for the acidification of the blood at high exercise intensities is two-fold: the high rates of ATP hydrolysis in the muscle release hydrogen ions, as they are co-transported out of the muscle into the blood via the monocarboxylate transporter, and also bicarbonate stores in the blood begin to be used up. This happens when lactate is produced faster than it can be removed (metabolized) in the muscle. When exercising at or below the lactate threshold, any lactate produced by the muscles is removed by the body without it building up (e.g., aerobic respiration). When exercising at or above the lactate threshold (e.g. anaerobic respiration), excess lactate can build up in tissue causing a lower pH and soreness, called acidosis. This excess lactate build-up decreases athletic ability during exercise as well tissue recovery after exercise.

Prior to exercise or activity the patient applies or wears a LLEC hydrogel device to his body, such as the upper body using a shirt, the lower body using pants, applying a hydrogel ointment to ankle, or a combination of the like. The hydrogel consists of integrated microparticles of a standard LLEC system. The LLEC system can be configured to penetrate into superficial muscle tissue under the hydrogel. The LLEC system increased cellular glucose uptake. Increased glucose uptake can result in greater mitochondrial activity and thus increased glucose utilization, providing more energy for cellular activity to remove lactic acid from muscle tissue. It has been shown that an increased cellular glucose utilization can also sustain anaerobic respiration for a longer period of time during exercise, thus increasing a person's lactate threshold. An increased lactate threshold prevents lactate from building-up in muscle tissue and strengthens sustainable athletic performance for longer periods of time.

Example 9

Three Dimensional Energy Source for Clothing, Prosthetics, or Medical Devices

The three-dimensional energy source can be used to supply power to low-energy devices worn as clothing, prosthetic devices, and medical devices. For example a clothing material can be constructed of a bioelectric hydrogel to comprise sensors to detect temperature of a patient's skin. The LLEC system of the hydrogel can be configured to supply power to the sensor detecting the skin temperature. Additionally, the energy source can be supplied by the clothing to a near by object requiring power such as a pacemaker under the chest tissue. In particular, the LLEC hydrogel system can be worn as a shirt and transmit power to a pacemaker directly under the skin.

In another example, a bioelectric hydrogel can be used to manufacture an electrical prosthetic. In particular, a prosthetic can be manufactured to comprise a hydrogel with a three-dimensional energy source to power the electronics or recharge the battery of the prosthetic.

In another example, a bioelectric hydrogel can be manufactured into a pacemaker. In particular, a pacemaker can be manufactured to comprise a hydrogel to provide power to the pacemaker for a specified period of time.

Example 10

Three Dimensional Energy Source for Cell Culture

Neuro cells and nerve ganglions are very difficult to grow in vitro. Current cellular medium cannot provide the appropriate energy or nutrients to sustain such cells in vitro. The energy environment present in a three dimensional energy source, such as the disclosed hydrogel, can make for a more stable environment for cellular growth. The addition of nutrients to the hydrogel cellular medium can make it possible to grow and maintain the neural cells and nerve ganglia in vitro.

The hydrogel can also be formed or shaped into a Petri dish. In particular, hydrogel can be configured to be a high viscosity and molded into a Petri dish for cellular culture. Specifically, the hydrogel Petri dish can provide a three dimensional energy source to the cultured medium being held by the Petri dish and make it possible to grow and maintain the neural cells and nerve ganglia in vitro.

Example 11

Treatment of Open Fracture

A 15-year old male suffers a grade-III open tibia-fibula fracture, leaving exposed bone and muscle. The wound is dressed with LLEC systems as described herein comprising a bioelectric device containing an array of biocompatible microcells and a hydrogel containing an array of biocompatible microcells. The wound heals without the need of muscle or skin grafts. The wound is also kept free from microbial contamination as a result of the broad-spectrum antimicrobial effect of the systems as disclosed herein.

Example 12

Treatment of an Insect Bite

A 25-year old male suffers numerous mosquito bites along his legs. A LLEC system including a pliable dressing material as described herein comprising a bioelectric device containing an array of biocompatible microcells and a hydrogel containing an array of biocompatible microcells is wrapped around his legs. The LLEC system reduces the swelling and eliminates the itching caused by the bites within 3 hours.

Example 13

Treatment of a Venomous Snake Bite

A 25-year old male suffers a venomous snake bite to his leg. Bleeding is stopped then the wound is dressed with a LLMC system comprising a bioelectric dressing containing an array of biocompatible microcells and a hydrogel containing an array of biocompatible microcells. The venom injected during the bite is neutralized. Over the next 2 weeks the wound heals. The wound is also kept free from microbial contamination as a result of the broad-spectrum antimicrobial effect of the wound management systems disclosed herein.

Example 14

Treatment of Diabetes

A 48-year old woman suffers from type 2 diabetes. To limit glucose excursions and lower serum glucose levels, LLEF systems comprising an array of biocompatible microcells and a hydrogel containing an array of biocompatible microcells are applied around the patient's abdomen and extremities. This increases cellular glucose uptake and reduces serum glucose levels, as well as moderating glucose excursions.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A hydrogel, comprising: a hydrophilic polymer base; and two or more biocompatible electrodes configured to generate at least one of a low level electric field (LLEF) and a low level electric current (LLEC), wherein the biocompatible electrodes comprise a first bioelectric element comprising a first microparticle formed from a first conductive material, and a second bioelectric element comprising a second microparticle formed from a second conductive material.

2. The hydrogel of claim 1, wherein the first conductive material and the second conductive material comprise the same material.

3. The hydrogel of claim 1, wherein the first bioelectric element and the second bioelectric element comprises a three dimensional matrix capable of defining at least one voltaic cell for spontaneously generating at least one electrical current with the conductive material of the first bioelectric element when the first and second bioelectric elements are introduced to an electrolytic solution.

4. The hydrogel of claim 3, wherein the first bioelectric element and the second bioelectric element each comprise a discrete circuit.

5. The hydrogel of claim 4, further comprising a power source.

6. The hydrogel of claim 5, wherein the first bioelectric element and the second bioelectric element spontaneously generate a LLEF.

7. The hydrogel of claim 6, wherein the first bioelectric element and the second bioelectric element spontaneously generate a LLEC when contacted with an electrolytic solution.

8. The hydrogel of claim 7, wherein the LLEC produces a microcurrent between 1 and 200 micro-amperes.

9. The hydrogel of claim 1, wherein the combination of the hydrophilic polymer base and the biocompatible electrodes is a low viscosity or a high viscosity.

10. The hydrogel of claim 1, wherein the first microparticles and the second microparticles are configured to be same specific gravity as the hydrophilic polymer base.

\* \* \* \* \*